(12) United States Patent
Mohanty

(10) Patent No.: US 11,796,537 B2
(45) Date of Patent: Oct. 24, 2023

(54) SEALED FLUID CHAMBER WITH PLANARIZATION FOR BIOMOLECULAR SENSORS AND RELATED METHODS

(71) Applicant: FemtoDx, Inc., Beverly Hills, CA (US)

(72) Inventor: Pritiraj Mohanty, Beverly Hills, CA (US)

(73) Assignee: FemtoDx, Inc., Beverly Hills, CA (US)

( * ) Notice: Subject to any disclaimer, the term of this patent is extended or adjusted under 35 U.S.C. 154(b) by 736 days.

(21) Appl. No.: 16/773,839

(22) Filed: Jan. 27, 2020

(65) Prior Publication Data
US 2020/0249225 A1    Aug. 6, 2020

Related U.S. Application Data

(60) Provisional application No. 62/799,206, filed on Jan. 31, 2019, provisional application No. 62/799,200, (Continued)

(51) Int. Cl.
*G01N 33/543*    (2006.01)
*G01N 27/414*    (2006.01)
(Continued)

(52) U.S. Cl.
CPC .... *G01N 33/5438* (2013.01); *B01L 3/502715* (2013.01); *B82Y 15/00* (2013.01); *G01N 27/12* (2013.01); *G01N 27/4146* (2013.01); *G01N 27/4148* (2013.01); *B01L 2300/041* (2013.01); *B01L 2300/046* (2013.01);
(Continued)

(58) Field of Classification Search
CPC ............... G01N 33/5438; G01N 27/12; G01N 27/4146; G01N 27/4148; G01N 27/4145; B01L 3/502715; B01L 2300/041; B01L 2300/046; B01L 2300/0627; B01L 2300/0645; B01L 2300/12; B01L 2200/027; B01L 2200/0689; B01L 3/502707; B82Y 15/00
See application file for complete search history.

(56) References Cited

U.S. PATENT DOCUMENTS

2016/0238553 A1* 8/2016 Shachar ............. G01N 27/4145

FOREIGN PATENT DOCUMENTS

WO    WO-2016145300 A1 * 9/2016
WO    WO-2017041056 A1 * 3/2017 ........... C12Q 1/6869

* cited by examiner

*Primary Examiner* — Dennis White
(74) *Attorney, Agent, or Firm* — Wolf, Greenfield & Sacks, P.C.

(57) ABSTRACT

The techniques relate to methods and apparatus for sealed fluid chambers. The device includes a sensor chip comprising a set of sensor elements configured to sense an analyte, and the set of sensor elements comprise an associated set of electrodes extending along the surface of the substrate. The device includes a fluid chamber comprising an edge proximate to the surface of the substrate, the fluid chamber comprising an inner portion in fluid communication with the set of sensor elements, wherein at least one electrodes extends from the inner portion of the chamber across the edge of the chamber and outside of the fluid chamber. The device includes a sealing member between the edge of the fluid chamber and the surface of the substrate such that the sealing member is disposed over at least a portion of the electrode that extends across the edge of the fluid chamber.

17 Claims, 15 Drawing Sheets

Related U.S. Application Data filed on Jan. 31, 2019, provisional application No. 62/799,194, filed on Jan. 31, 2019.

(51) Int. Cl.
    *B01L 3/00*     (2006.01)
    *G01N 27/12*     (2006.01)
    *B82Y 15/00*     (2011.01)

(52) U.S. Cl.
    CPC .............. *B01L 2300/0627* (2013.01); *B01L 2300/0645* (2013.01); *B01L 2300/12* (2013.01)

SEALED FLUID CHAMBER WITH PLANARIZATION FOR BIOMOLECULAR SENSORS AND RELATED METHODS

RELATED APPLICATIONS

This Application claims priority under 35 U.S.C. § 119(e) to U.S. Provisional Application Ser. No. 62/799,194, filed Jan. 31, 2019 and entitled "SEALED FLUID CHAMBER WITH THROUGH SEMICONDUCTOR VIAS FOR BIOMOLECULAR SENSORS," U.S. Provisional Application Ser. No. 62/799,200, filed Jan. 31, 2019 and entitled "SEALED FLUID CHAMBER WITH PLANARIZATION FOR BIOMOLECULAR SENSORS AND RELATED METHODS," and U.S. Provisional Application Ser. No. 62/799,206, filed Jan. 31, 2019 and entitled "MULTI-CHIP MODULE FOR NANOWIRE BIOSENSORS AND RELATED METHODS," which are hereby incorporated by reference in their entirety.

FIELD

The techniques described herein relate generally to methods and apparatus for nanochannel-based sensors used to sense chemical or biological species, and in particular to sealed fluid chambers disposed over semiconductor nanowire-based sensors employing a planarized layer and related methods.

BACKGROUND

Chemical or biological sensors can include nanowires and/or other small-scale electrical devices that essentially serve as sensitive transducers that convert chemical activity of interest into corresponding electrical signals that can be used to accurately represent the chemical activity. The nanosensors can include one or more nanowires (e.g., which may have a tubular form). The nanowires can be fabricated such that once functionalized, their surface will interact with adjacent molecular entities, such as chemical species. The interaction of the nanowires with molecular entities can induce a change in a property (such as conductance) of the nanowire.

SUMMARY

Biomolecular sensors are useful for detecting a variety of biological molecules such as proteins, viruses, disease markers, and other organic compounds. For many sensing applications, it can be beneficial to employ sensors having high sensitivity to a species of interest. Sensors with high sensitivity can be used to detect much smaller amounts or concentrations of the species, which may be necessary or desirable in some applications, and/or such sensors can provide a high signal-to-noise ratio and thus improve the quality of measurements that are taken using the sensor.

A biomolecular sensor generally consists of a specific sensor region that must be placed in fluid contact with or otherwise exposed to a biological sample. Biological samples are often fluids, and when placed over the sensor region the fluid can spread over an area much larger than the sensor region. The inventors have appreciated that it is desirable to confine the sample near the sensor region, which can improve biosensors (e.g., by requiring less sample, improving analyte detection, etc.). The techniques described herein provide fluid chambers that can confine the fluid sample around the sensor region. The techniques include using a sealing o-ring to seal the fluid chamber to the substrate that contains the sensor. The fluid chamber may contain input and/or output holes for creating pressure-induced flow across the sensor.

In some embodiments, the techniques include using through silicon vias (TSVs) to create electrical connections to the sensors disposed within the fluidic chambers. The sensors are usually at least partially disposed on a top surface of the substrate to which the fluid chamber is mounted. The edge of the fluid chamber can be connected to the surface of the substrate using a sealing member, such as an o-ring, to create a leak-resistant seal between the fluid chamber and the substrate (e.g., a leak-proof seal). To create electrical contacts to the sensors that do not interfere with sealing the fluid chamber to the top surface of the substrate, TSVs can be used to create electrical connections to the sensors from the bottom side of the substrate. The TSVs can include a dielectric spacer that insulates the TSVs from the substrate to avoid electrical connections between the TSVs and the substrate.

Some embodiments relate to a device, comprising a sensor chip comprising a set of sensor elements at least partially disposed on a first side of a substrate, wherein each sensor element of the set of sensor elements is configured to sense an analyte and comprises an associated set of through silicon vias (TSVs), each TSV of the set of TSVs extending from an associated portion of the sensor element through the substrate to a second side of the substrate that is opposite the first side, a fluid chamber proximate to the first side of the substrate and comprising an inner portion in fluid communication with the set of sensor elements, and a sealing member between the fluid chamber and the first side of the substrate.

In some examples, the set of sensor elements comprise a silicon sensor. The set of sensor elements can include a plurality of silicon sensors. A sensor element of each set of sensor elements can include a source, a drain, and at least one nanowire in electrical communication with the source and the drain. The set of TSVs can include a first TSV in electrical communication with the source, and a second TSV in electrical communication with the drain.

In some examples, the set of sensor elements are functionalized to detect an analyte.

In some examples, the device further includes a fluid channel in fluid communication with the fluid chamber. The fluid channel can be a tube that fluidly connects a fluid reservoir to the fluid chamber. The device can further include a second fluid channel in fluid communication with the fluid chamber. The fluid channel can be an input fluid channel and the second fluid channel can be an output fluid channel.

In some examples, the sealing member is an o-ring. The o-ring can include a material selected from the group consisting of a permanent glue, a gel, a polymer, rubber and silicone. The o-ring can include a first portion substantially in contact with the first side of the substrate. The o-ring can include a second portion substantially in contact with an edge of the fluid chamber. The o-ring can include a leak-resistant seal between the top surface of the substrate and the fluid chamber.

In some examples, a TSV from the set of TSVs comprises a top electrode disposed at least partially on the first side of the substrate, wherein the top electrode is in electrical communication with at least one sensor element of the set of sensor elements. The TSV can further include a conductive pathway in electrical communication with the top electrode, wherein the conductive pathway extends through the substrate. The conductive pathway can include a metal. The TSV can further include a bonding pad proximate to the second side of the substrate. The TSV can further include a dielectric spacer disposed between the conductive pathway and the substrate. The dielectric spacer can be disposed between the top electrode and the substrate, between the bonding pad and the substrate, or both.

In some embodiments, the sensors may include one or more electrodes on the top surface of the substrate. Such electrodes can create discontinuities in the surface of the substrate, such as at edges of the electrodes (e.g., which may be sharp, bumpy, of different thicknesses, etc.). If the edge of the fluidic chamber is mounted over discontinuities in the substrate surface, it can cause micro leaks between the seal of the fluidic chamber and the substrate. Some embodiments include a sealing member that includes a planarized ring (e.g., of insulating material) that is disposed around the location where the edge of the fluidic chamber is mounted to the substrate (e.g., where the o-ring makes contact with the substrate). The planarized ring creates a smooth surface for connecting the o-ring to the substrate to create a leak-resistant (e.g., leak-proof) seal between the fluidic chamber and the substrate.

Some embodiments relate to a device, comprising a sensor chip comprising a set of sensor elements at least partially disposed on a surface of a substrate, wherein each sensor element of the set of sensor elements is configured to sense an analyte, and the set of sensor elements comprise an associated set of electrodes extending along the surface of the substrate, a fluid chamber comprising an edge proximate to the surface of the substrate, the fluid chamber comprising an inner portion in fluid communication with the set of sensor elements, wherein at least one electrode of the set of electrodes extends from the inner portion of the chamber across the edge of the chamber and outside of the fluid chamber, and a sealing member between the edge of the fluid chamber and the surface of the substrate such that the sealing member is disposed over at least a portion of the electrode extends across the edge of the fluid chamber.

In some examples, the set of sensor elements comprise a silicon sensor. The set of sensor elements can include a plurality of silicon sensors. A sensor element of each set of sensor elements can include a source, a drain, and at least one nanowire in electrical communication with the source and the drain. The set of electrodes can include a first electrode in electrical communication with the source, and a second electrode in electrical communication with the drain.

In some examples, the set of sensor elements are functionalized to detect an analyte.

In some examples, the device further includes a fluid channel in fluid communication with the fluid chamber. The fluid channel can be a tube that fluidly connects a fluid reservoir to the fluid chamber. The device can further include a second fluid channel in fluid communication with the fluid chamber. The fluid channel is an input fluid channel and the second fluid channel is an output fluid channel.

In some examples, the sealing member comprises a planarized layer disposed on the surface of the substrate and the portion of the electrode extending across the edge of the fluid chamber. The planarized layer can include a material selected from the group consisting of an oxide, a polymer, and a metal. The sealing member can include a bottom portion contoured over the surface of the substrate and the portion of the electrode extending across the edge of the fluid chamber. The sealing member can include an o-ring. The o-ring can be disposed between the planarized layer and the edge of the fluid chamber. The o-ring can include a material selected from the group consisting of a permanent glue, a gel, a polymer, rubber and silicone. The planarized layer and o-ring can include a leak-resistant seal between the edge of the fluid chamber and the top surface of the substrate and the portion of the electrode.

Some embodiments relate to multichip modules for nanowire biosensors. Individual chip sensors are typically sensitive to detecting a single molecular species. In many cases, it is desirable to detect multiple molecular species, often of a single sample (e.g., to increase diagnostic power and/or avoid requiring a large quantity of the sample). The techniques described herein provide a multi-chip module that includes a plurality of sensor chips. The sensor chips can be the same and/or different chips with the same and/or different functional purposes. Such an arrangement can allow for detecting multiple molecular species in a single sample and/or for performing other functions on the sample (e.g., filtering, temperature testing, etc.). Some embodiments include separate fluidic chambers for different sensor chips, which can be sealed to the chips using the techniques described herein. Some embodiments use a fluidic chamber for a plurality of sensor chips, which can also be sealed to the chips (e.g., including over inter-chip boundaries) using the techniques described herein.

Some embodiments relate to a device, comprising a plurality of sensor chips, each sensor chip comprising a set of sensor elements, wherein each sensor element of the set of sensor elements is configured to sense an analyte, at least one fluid chamber comprising an inner portion proximate to, and in fluid communication with, at least one of the plurality of sensor chips, and a sealing member between the at least one fluid chamber and the at least one of the plurality of sensor chips.

In some examples, the set of sensor elements of each of the plurality of sensor chips comprise a silicon sensor. The set of sensor elements of each of the plurality of sensor chips can include a plurality of silicon sensors. A sensor element of each set of sensor elements can include a source, a drain, and at least one nanowire in electrical communication with the source and the drain.

In some examples, a first set of sensor elements of a first sensor chip of the plurality of sensor chips is functionalized to detect a first analyte, and a second set of sensor elements of a second sensor chip of the plurality of sensor chips is functionalized to detect a second analyte different than the first analyte.

In some examples, the at least one fluid chamber comprises a first fluid chamber in fluid communication with at least a first sensor chip of the plurality of sensor chips, wherein the sealing member is between the first fluid chamber and at least the first sensor chip, and a second fluid chamber in fluid communication with at least a second sensor chip of the plurality of sensor chips, comprising a second sealing member between the second fluid chamber and at least the second sensor chip. The device can further include a fluid connector between the first fluid chamber and the second fluid chamber. The fluid connector can be a tube that fluidly connects the first fluid chamber to the second fluid chamber.

In some examples, the at least one fluid chamber can include a separate fluid chamber for each of the plurality of sensor chips, and the sealing member comprises a separate sealing member between each separate fluid chamber and associated sensor chip of the plurality of sensor chips. Each pair of the separate fluid chambers can include a fluid connector between the pair of separate fluid chambers. The fluid connector can be a tube that fluidly connects the pair of separate fluid chambers.

In some examples, the plurality of sensor chips are arranged side-by-side, such that each sensor chip comprises an interchip seam between the sensor chip and at least one neighboring sensor chip, and the at least one fluid chamber comprises a single fluid chamber in fluid communication with all of the plurality of sensor chips, and the sealing member is between the single fluid chamber and the plurality of sensor chips, such that the sealing member is sealed over the interchip seams between the plurality of sensor chips.

In some examples, the plurality of sensor chips are integrated onto a single substrate.

In some examples, the sealing member is an o-ring.

In some examples, the fluid chamber comprises an input and an output. The input can include an input channel in fluid communication with the fluid chamber, and the output can include an output channel in fluid communication with the fluid chamber.

Some embodiments relate to a method of sensing at least one analyte, comprising introducing a fluid sample into at least one fluid chamber comprising an inner portion proximate to, and in fluid communication with, at least one of a plurality of sensor chips, each sensor chip comprising a set of sensor elements, wherein each sensor element of the set of sensor elements is configured to sense an analyte and a sealing member is disposed between the at least one fluid chamber and the at least one of the plurality of sensor chips, electrically driving at least a first set of sensor elements of at least one of the plurality of sensor chips in fluid communication with the fluid sample, and processing at least one electrical signal received from the first set of sensor elements to determine data indicative of whether the analyte is present in the fluid sample.

In some examples, electrically driving the at least first set of sensor elements comprises applying an alternating current modulated on a direct current bias across at least one nanowire of a sensor element of the set of sensor elements.

In some examples, the at least one nanowire comprises a set of surface binding sites configured to bind to one or more charged molecules in the fluid sample, such that the sensor element is configured to operate as a field effect transistor.

In some examples, processing the at least one electrical signal comprises comparing the electrical signal with a control signal to determine the data indicative of whether the analyte is present in the fluid sample.

FIGURES

In the drawings, each identical or nearly identical component that is illustrated in various figures is represented by a like reference character. For purposes of clarity, not every component may be labeled in every drawing. The drawings are not necessarily drawn to scale, with emphasis instead being placed on illustrating various aspects of the techniques and devices described herein.

FIG. 1A is a schematic diagram illustrating the use of a sensor device used to detect species in an analyte solution, according to some examples.

FIG. 1B (with views (a)-(d)) depicts a nanochannel-based sensing element that can be used in the circuit of FIG. 1A, according to some examples.

DETAILED DESCRIPTION

Nanochannel-based sensors can be designed to analyze a fluid, such as for testing for the presence of an analyte carried by or ensconced in a fluid sample. Various fluid samples can be used with biomolecular sensors. In some embodiments, the samples are a bodily fluid, such as blood, lymph, urine, saliva, and/or the like. In some embodiments, the fluid is a manufactured fluid. In some embodiments, the fluid is a deionized or otherwise modified biological solution. In some embodiments, the samples are artificial samples, such as a sample with a given analyte concentration.

The concentration of the analyte can be determined in a controlled environment based on various measurements, such as measurements taken of air, measurements taken using a blank liquid (without the analyte), and measurements taken using a reference or test liquid that may (or may not) contain the analyte. The techniques described herein provide a sealed fluidic chamber that can be used to enhance the performance of biomolecular sensor devices. In some embodiments, fluid chamber can be sealed to a substrate using a sealing member (e.g., an o-ring). Leak-resistant TSVs can be used to connect to sensor(s) from the opposite side of the substrate. Such techniques can be used to manage the volume and flow of the fluid in a biosensor, which can significantly increase performance of the biosensor.

Large biomolecules, such as proteins or virus fragments (e.g., which can include nanoparticles, with size ranging from 10-5000 nm), can be considered dielectric nanoparticles. In some embodiments, the biomolecules are naturally uncharged. In certain embodiments, the biomolecules are charged, and attract free ions in solution to become effectively neutral. In such embodiments, the size of the dielectric particle is increased from the size of the bare particle by the Debye length, e.g., typically on the order of 1-10 nm.

Figure 1A:
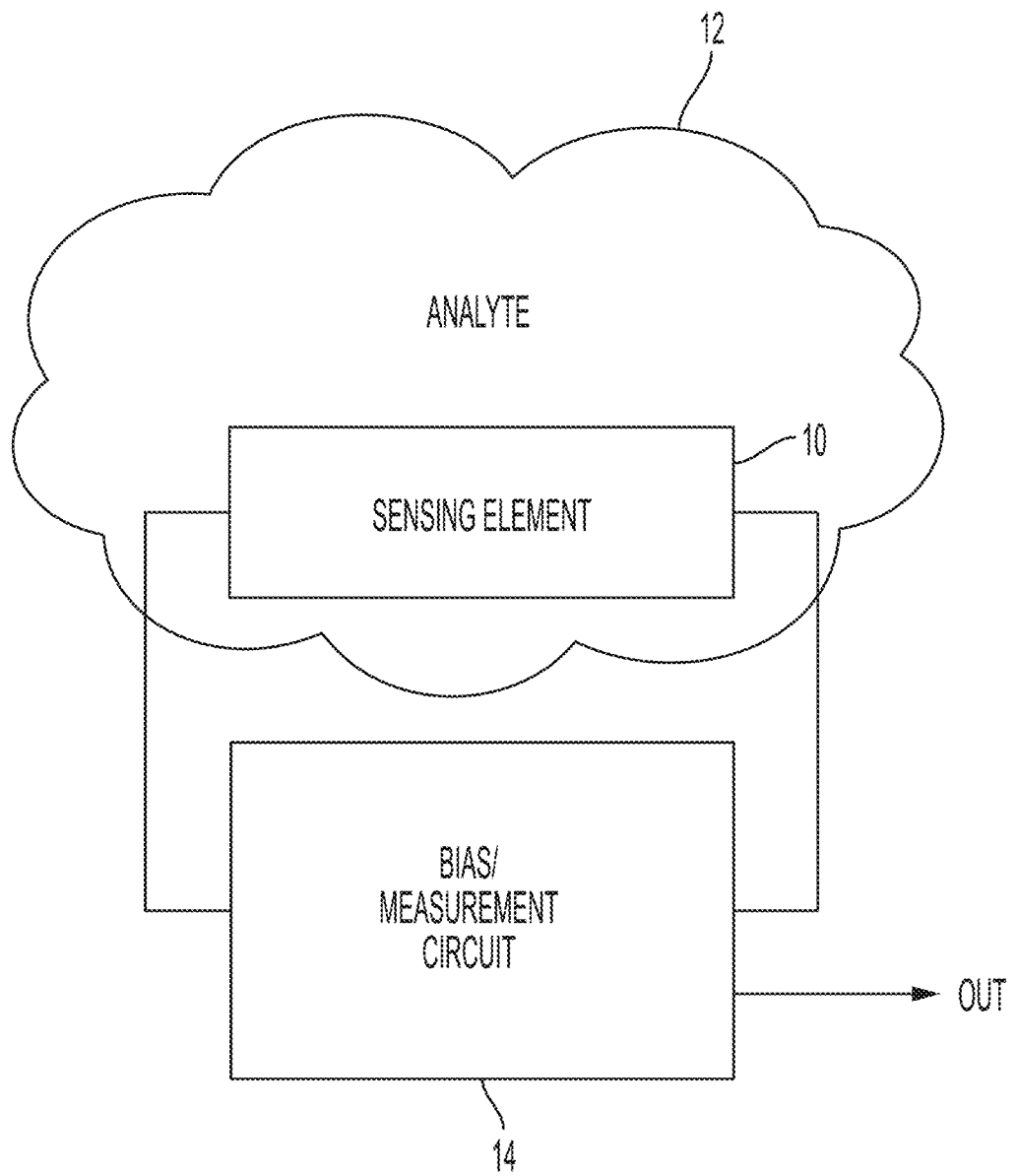
FIG. 1C depicts a sensor employing an array of nanochannels, according to some examples.
FIGS. 1D-1E are exemplary schematic diagrams of a semiconductor-based biomolecular analyte sensor, according to some examples.

Various types of molecular sensors, such as field effect biomolecule sensors (e.g., nanowire field effect transistors), can be used to detect biomolecules of interest. In FIG. 1A, a sensing element 10 is exposed to chemical or biological species (analyte) in an analyte solution 12. The sensing element 10 has connections to a bias/measurement circuit 14 that provides a bias voltage to the sensing element 10 and measures the differential conductance of the sensing element 10 (e.g., the small-signal change of conductance with respect to bias voltage). The differential conductance of the device is measured by applying a small modulation of bias voltage to generate a value of an output signal (OUT) that provides information about the chemical or biological species of interest in the analyte solution 12, for example a simple presence/absence indication or a multi-valued indication representing a concentration of the species in the analyte solution 12.

Suitable sensing elements (e.g., including semiconductor nanowires) and sensing technologies have been described in commonly-owned International Publication Number WO 2016/089,453, U.S. Pat. No. 10,378,044 and U.S. Publication No. 2014/0030747, each of which are incorporated herein by reference in their entireties.

The sensing element 12 includes one or more elongated conductors of a semiconductor material such as silicon, which may be doped with impurities to achieve desired electrical characteristics. The dimensions of a channel can be sufficiently small (e.g., nanoscale) such that chemical/electrical activity on the channel surface can have a much more pronounced effect on electrical operation than in larger devices. Such nanoscale channels may be referred to as nanochannels herein. In some embodiments, the sensing element 12 has one or more constituent nanochannels having a cross-sectional dimension of less than about 150 nm (nanometers), and even more preferably less than about 100 nm.

As described herein, the surface of the sensing element 12 can be functionalized by using a series of chemical reactions to incorporate receptors or sites for chemical interaction with the species of interest in the analyte solution 12. As a result of this interaction, the charge distribution, or surface potential, of the surface of the sensing element 12 changes in a corresponding manner. Such a change of surface potential can alter the conductivity of the sensing element 10 in a way that is detected and measured by the bias/measurement circuit 14. Thus, the sensing element 12 can operate as a field-effect device, since the channel conductivity can be affected by a localized electric field related to the surface potential or surface charge density. The measured differential conductance values can be converted into values representing the property of interest (e.g., the presence or concentration of species), based on known relationships as may have been established in a separate calibration procedure, for example.

Figure 1B:
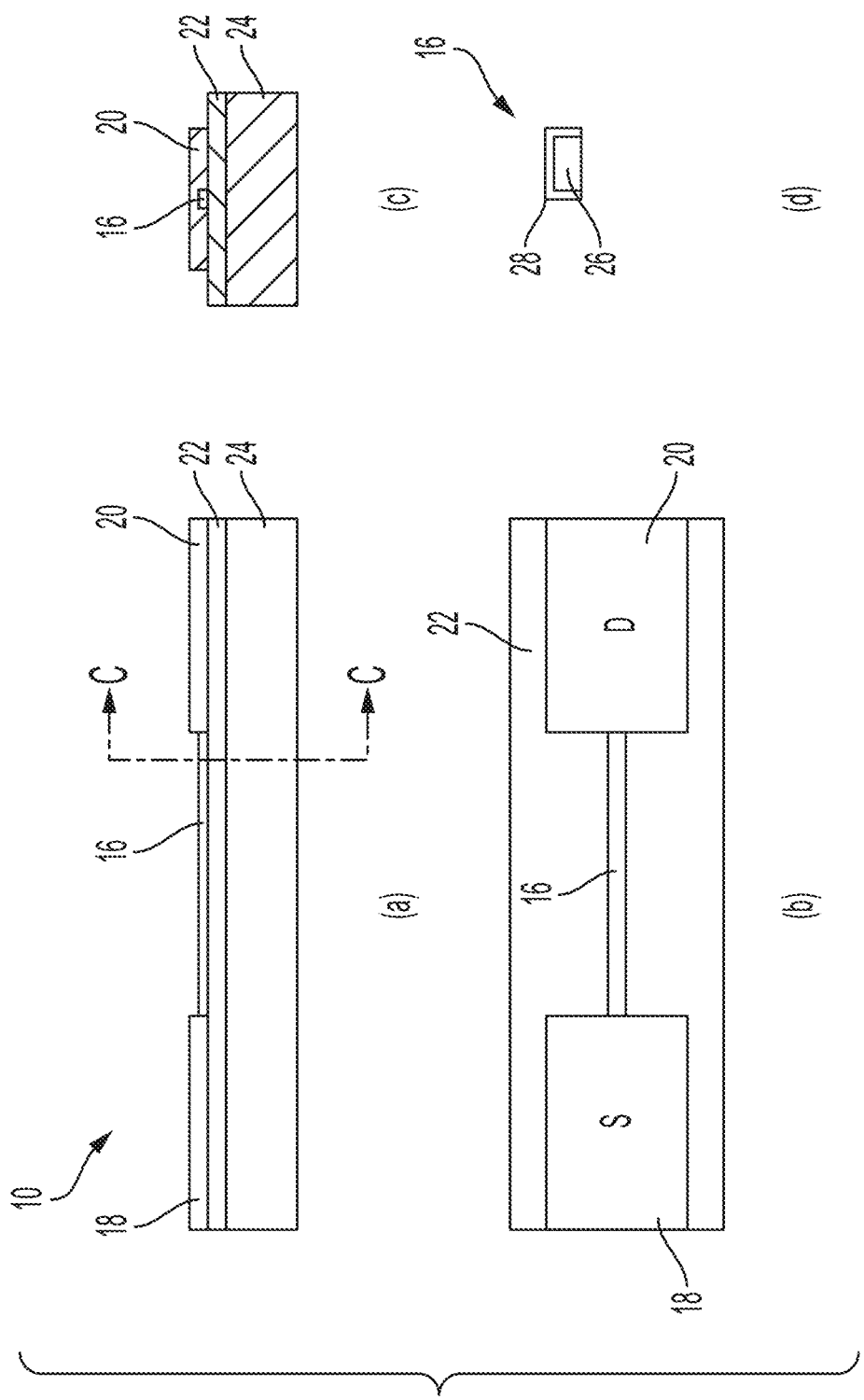

FIG. 1B shows a sensing element 10 according to one example. As shown in the side view (a) of FIG. 1B, a silicon nanochannel 16 extends between a source (S) contact 18 and a drain (D) contact 20, all formed on an insulating oxide layer 22 above a silicon substrate 24. View (b) of FIG. 1B is a top view showing the narrow elongated nanochannel 16 extending between the wider source and drain contacts 18, 20, which are formed of a conductive material such as gold-plated titanium for example. View (c) of FIG. 1B shows the cross-sectional view in the plane C-C of view (a). View (d) of FIG. 1B shows the cross section of the nanochannel 16 in more detail. In the illustrated embodiment, the nanochannel 16 includes an inner silicon member 26 and an outer oxide layer 28 such as aluminum oxide.

Figure 1C:
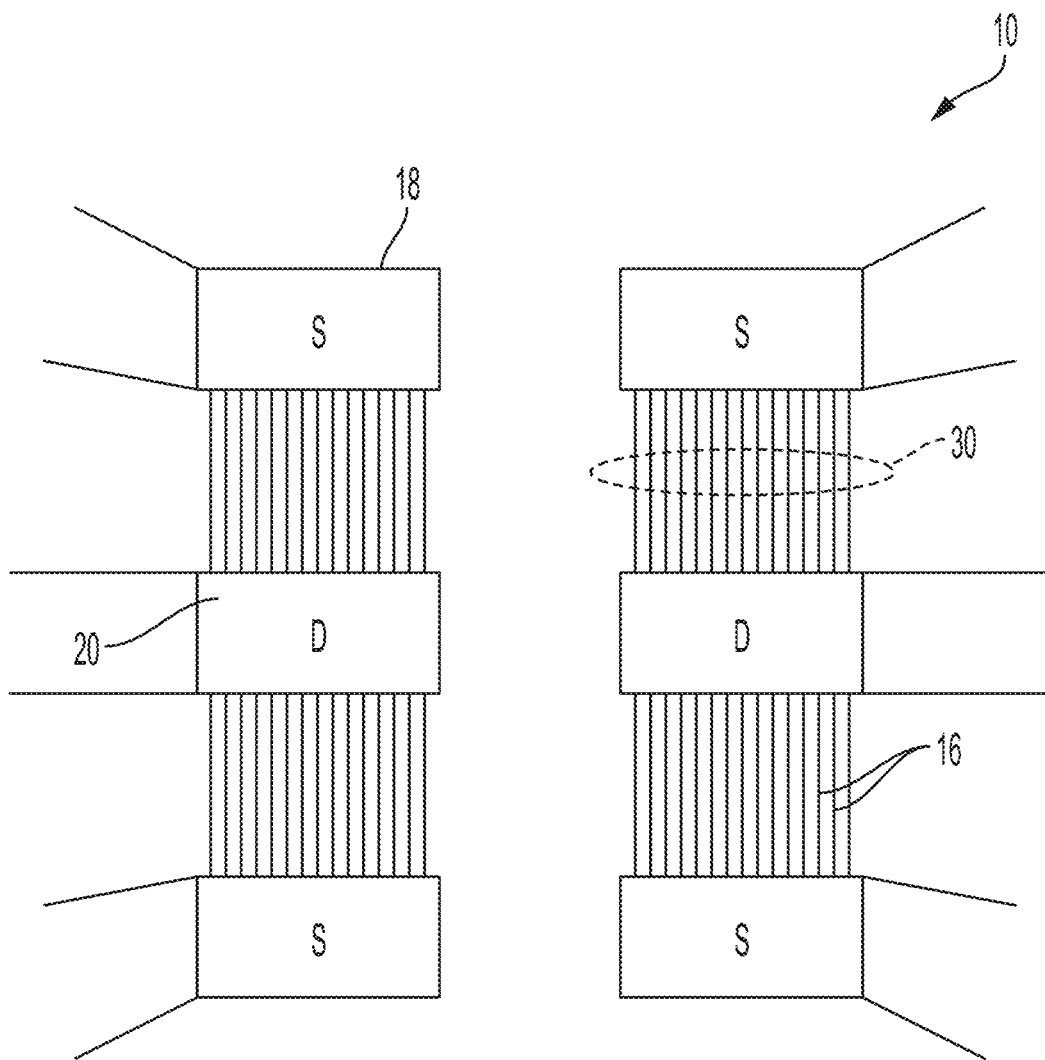

FIG. 1C shows a sensing element 10 employing an array of nanochannels 16, which in the illustrated example are arranged into four sets 30, each set including approximately twenty parallel nanochannels 16 extending between respective source and drain contacts 18, 20. By utilizing arrays of nanochannels 16 such as shown, greater signal strength (current) can be obtained, which can improve the signal-to-noise ratio of the sensing element 10. To obtain fully parallel operation, the source contacts 18 are all connected together by separate electrical conductors, and likewise the drain contacts 20 are connected together by separate electrical conductors. Other configurations are of course possible. For example, each set 30 may be functionalized differently so as to react to different species which may be present in the analyte solution 12, enabling an assay-like operation. In such configurations, it should be understood that each set 30 has separate connections to the bias/measurement circuit 14 to provide for independent operation.

The sensing element 10 may be made by a variety of techniques employing generally known semiconductor manufacturing equipment and methods. In some embodiments, Silicon-on-Insulator (SOI) wafers are employed. A starting SOI wafer may have a device layer thickness of 100 nm and oxide layer thickness of 380 nm, on a 600 μm boron-doped substrate, with a device-layer volume resistivity of 10-20 Ω-cm. After patterning the nanochannel channels and the electrodes (e.g., in separate steps), the structure can be etched out with an anisotropic reactive-ion etch (RIE). This process can expose the three surfaces (top and sides) of the silicon nanochannels 16 along the longitudinal direction, resulting in increased surface-to-volume ratio. A layer of $Al_2O_3$ (e.g., approximately 5 to 15 nm thick) can be grown using atomic layer deposition (ALD). Selective response to specific biological or chemical species can be realized by fabricating the nanochannels 16 such that once functionalized, the nanochannels 16 react to one or more analytes. In use, a flow cell, such as a machined plastic flow cell, can be employed. For example, a machined plastic flow cell can be fitted to the device and sealed with silicone gel, with the sensing element 10 bathed in a fluid volume (of about 30 μL for example), connected to a syringe pump.

In some embodiments, the sensing element 10 may include other control elements or gates adjacent to the nanochannels 16. For example, the sensing element 10 can include a top gate, which can be a conductive element formed along the top of each nanochannel 16. Such a top gate may be useful for testing, characterization, and/or in some applications during use, to provide a way to tune the conductance of the sensing element in a desired manner. As another example, the sensing element 10 may include one or more side gates formed alongside each nanochannel 16 immediately adjacent to the oxide layer 28, which can be used for similar purposes as a top gate. As a further example, in some embodiments the sensing element 10 can include a temperature sensor (e.g., disposed near the nanochannels). The system can use measurements from the temperature sensor to modify the system operations. For example, the circuitry can be configured to adjust how the system maps measured nanowire conductances to the concentration of an analyte.

Biomolecule sensors, such as the nanowire field effect transistors described above as well as other molecular sensors, are used to detect biomolecules of interest. Such molecular detection, where the presence of a specific molecule can be determined, can be useful for a variety of applications, including cancer detection, disease verification, and other medical and biological applications. In some embodiments, as described above the sensor component consists of a binding molecule attached to the surface of a semiconducting material (e.g., functionalized on the surface). In some embodiments, the semiconductor is patterned into nanowires. In some embodiments, bottom-up chemically-grown nanowires and micro/nano-structures are placed on top of a semiconductor substrate. In some embodiments, the semiconductor material is silicon, germanium, a III-V semiconductor, and/or the like. The sensor region can be generally approximately 10 microns by 10 microns in area. In some embodiments, the sensor region is larger. In some embodiments, the sensor region is a single nanowire approximately 50 nm by 5 microns.

The binding molecules, which can also be referred to as detectors, can be designed to be particle-specific, such that only one specific particle (the analyte) will bind to a given detector. In some embodiments, the detector is an antibody. In some embodiments, the detector is a DNA or RNA fragment. In some embodiments, the analyte is a protein. In some embodiments, the analyte is a virus particle. It should be appreciated that the techniques described herein can be used in conjunction with any possible detector and analyte species combinations.

Figure 1D:
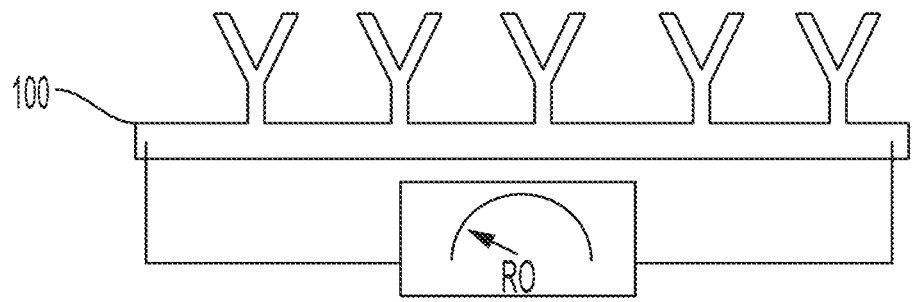
Figure 1E:
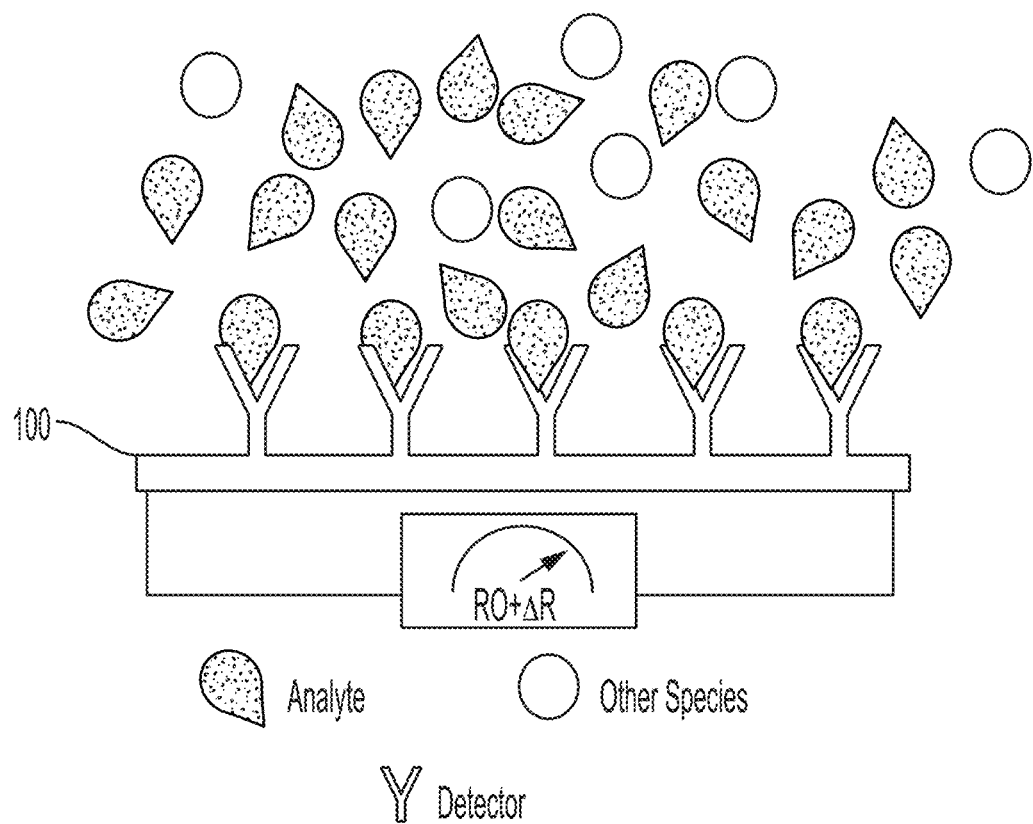

FIGS. 1D-1E are schematic diagrams of a general semiconductor-based biomolecular analyte sensor, according to some embodiments. As shown in FIG. 1E, binding of the specific analyte to the detector molecule results in a change in resistance of the semiconductor 100 relative to the bare state, as shown in FIG. 1D. When the analyte binds to the detector, it is held close to the substrate and no longer migrates within the fluid containing the analyte and other species. The binding of the analyte causes a measurable change in physical properties of the semiconductor. In some embodiments, a measured resistance (or conductance) change $\Delta R$ (or $\Delta G$) indicates the presence of the analyte, as illustrated in FIG. 1D (showing R0) and 1E (showing R0+$\Delta R$). In some embodiments, the analyte charge causes the change in conductivity. In some embodiments, structural changes in the detector molecule upon binding cause the measurable changes. In some embodiments, the change is due to electrical gating by the analyte. In some embodiments, the change is due to a change in the surface plasmon resonance. In some embodiments, the conductance change can be generally detected electrically by applying an electric current to the sensor and measuring a change in voltage. The application of currents and measuring of voltages can be performed using metal electrodes that attach to the semiconductor sensor, as described further herein.

The inventors have appreciated that various aspects of a fluidic sample can affect biosensor performance. For example, the sample may degrade when exposed to air. Additionally or alternatively, the total volume of fluid that interacts with the sensor can limit the sensitivity of the sensor. Therefore, the inventors have appreciated that techniques for controlling aspects of the fluid, such as the fluid volume, fluid confinement, and/or interaction of the fluid with surroundings, can be important for enhancing biomolecule sensor performance. However, challenges for biosensor design can include controlled fluid confinement, fluid volume, and/or fluid flow. For example, many sensors often use a small drop of biological fluid, such as blood, placed directly on the sensor region. This drop is then free to spread, evaporate, and/or otherwise deform, which can result in an incorrect detection and/or reduced sensitivity of detection. Additionally or alternatively, if the drop does not spread, sensitivity of the sensor may be reduced due to the fluid being stationary. Furthermore, removing the fluid, either for cleaning or calibration, can be time consuming or detrimental to future use of the sensor (e.g., due to inadvertently damaging the sensor).

The inventors have also appreciated that it can be desirable to replace the sample in the sensor. For example, to sense for an analyte in a solution, some biosensors compare electrical measurements when exposed to the sample with electrical measurements when exposed to a reference. Such reference-based testing can be conducted by replacing the sample with the reference, while keeping temperature and other external parameters as constant as possible. For proper testing, it is often desirable that the reference fluid completely replaces the sample. However, removing the sample with absorptive or evaporative techniques may leave residues, may be costly, and/or may be time-consuming. Therefore, the inventors have appreciated that it is desirable to develop techniques to easily replace one fluid with another, which can enhance sensor performance.

The inventors have further appreciated that sensor performance can be improved by flowing the fluid sample across the sensor, which can allow a larger total volume of fluid to interact with the sensor. Pressure-induced flow, which does not introduce extra electrical fields that may affect sensor measurement, often requires confining the fluid within a specific volume. It can also be desirable to control the flow velocity to prevent sensor degradation.

The techniques described herein can address such deficiencies and/or other deficiencies by providing a sealed fluid chamber attached to the sensor substrate into which fluid is pumped. In some embodiments, a tight seal can be achieved between the fluid chamber and substrate by using an o-ring seal and Through Silicon Vias (TSV). The o-ring can be used to join the edge of the fluid chamber to the substrate. TSVs can, for example, be used to avoid creating discontinuities in the substrate topography that may otherwise be caused by depositing electrodes on the surface of the substrate. In some embodiments, the fluid chamber includes holes, such as input and/or output holes through which fluid can be injected and/or removed. The fluid chamber can be attached to any pressure flow inducing device, fluid reservoir, and/or the like to introduce and flow a fluid through the fluid chamber. In some embodiments, the fluid is introduced using a syringe. In some embodiments, the fluid is introduced using an automated mechanical pump.

Figure 2:
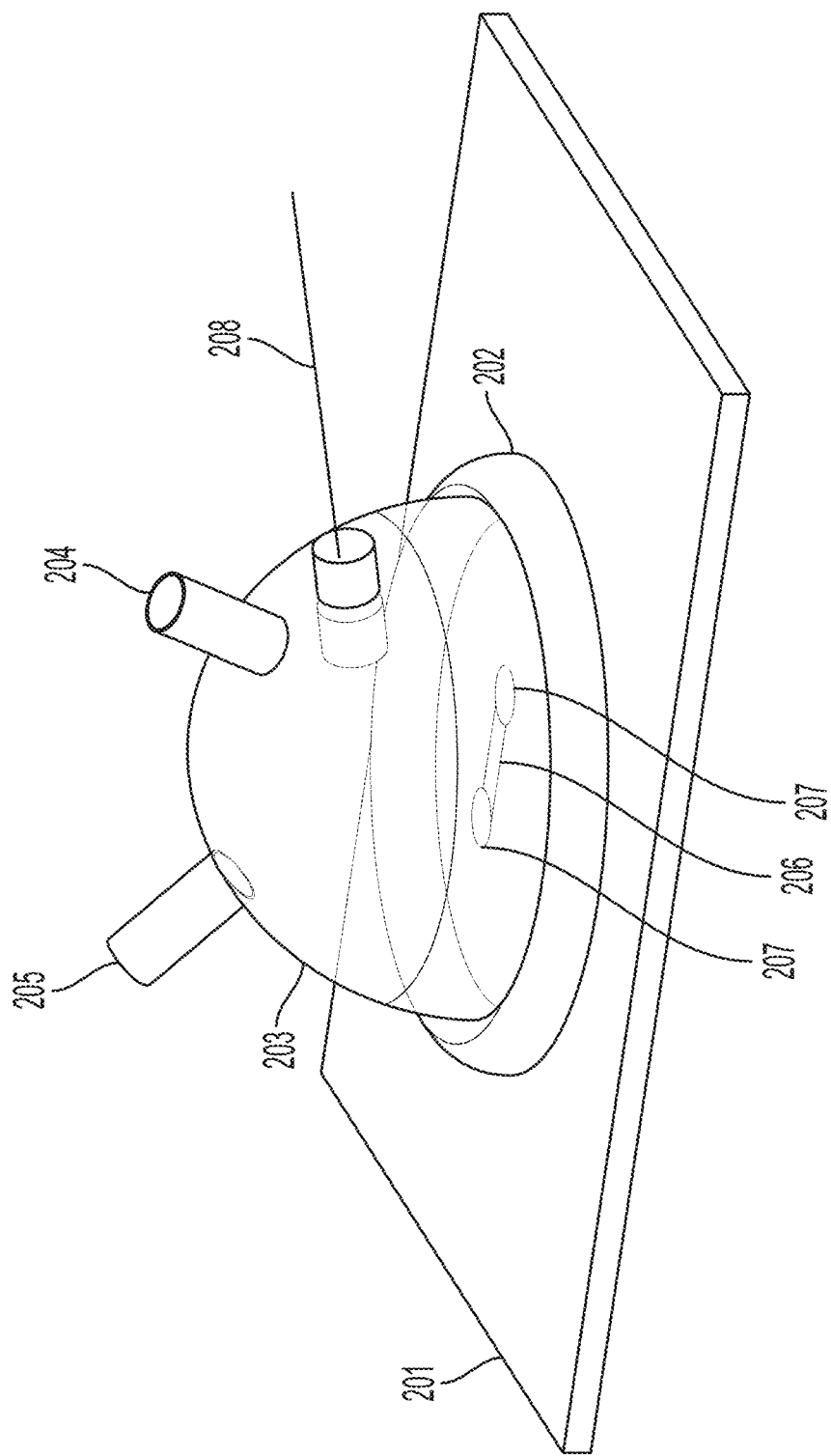
FIG. 2 is a diagram of a perspective view of an exemplary sensor with a fluid chamber mounted over a sensor that utilizes TSVs to connect to the sensor, according to some embodiments.

FIG. 2 is a diagram of an exemplary perspective view of a fluid chamber sealed on a sensor, according to some embodiments. An o-ring seal 202 is adhered to the substrate 201, forming a tight seal between the edge of the chamber 203 and the o-ring 202 so that no fluid can escape between the chamber 203 and the substrate 201. The example shown in FIG. 2 includes an input channel 204 and an output channel 205 attached to the chamber. The chamber includes holes that allow fluid to be input and output through the input channel 204 and output channel 205. The sensor 206 is disposed in the center of the chamber 203, with electrical leads that exit downward through TSVs 207. A reference electrode 208 may be added through the chamber wall.

The adhesion of the o-ring 202 to the substrate 201 is tight enough such that fluid cannot escape. In some embodiments, the adhesion is created with a permanent glue. In some embodiments, the adhesion is created by a reusable gel or polymer. In some embodiments, the o-ring 202 is rubber. In some embodiments, the o-ring is silicone. While some examples have been provided, it should be appreciated that the techniques are not limited in terms of adhesion substances or o-ring materials.

An edge of the chamber 203 is attached to the o-ring 202 to create the chamber within which the fluid can flow. The chamber 203 can be made from various materials. In some embodiments, the chamber 203 is made of a polymer such as polyethylene. In some embodiments, the chamber 203 is glass. In some embodiments the chamber 203 is a metal. The chamber 203 can be of various shapes. In some embodiments, the chamber 203 is a hemisphere as shown in FIG. 2. In certain embodiments, the chamber is a hemiellipsoid. In some embodiments, the chamber 203 is in the form of a cylinder. The chamber 203 and o-ring 202 can be fabricated using one or more fabrication steps. In some embodiments, the surface is adhered to the o-ring 202 in a separate step than the step used to connect the chamber 203 to the o-ring 202. In some embodiments, the o-ring 202 and chamber 203 are manufactured to be attached to each other. While some exemplary aspects of the chamber 203 have been described, it should be appreciated that the techniques are not limited in terms of chamber shapes, materials, or chamber adhesion methods.

The o-ring 202 can be designed so that the o-ring 202 is large enough to encompass the entire sensor region. In some embodiments, the o-ring 202 has a diameter greater than 100 microns. In some embodiments, the o-ring 202 has a diameter greater than 1 mm. In some embodiments, the diameter is larger than 1 cm. The o-ring can be of different shapes (e.g., sized to match the shape of the edge of the chamber). In some embodiments, the o-ring 202 is circular. In some embodiments, the o-ring 202 is elliptical. In some embodiments, the o-ring 202 is a square. While some examples are provided herein, the techniques are not limited in terms of o-ring sizes and shapes.

In some embodiments, it is desirable to flow fluid through the chamber. As shown in the example of FIG. 2, the chamber 203 has holes connected to flow channels 204 and 205 so that fluid can be injected and flowed over the sensor. The flow channels can be disposed at various locations of the chamber 203 other than as shown in FIG. 2. In some embodiments, the holes are at opposite sides of the chamber 203. In some embodiments, one hole is at the top of the chamber 203 and one hole is on the side of the chamber 203. It should be understood that the techniques are not limited in terms of hole placement geometries.

As shown in FIG. 2, TSVs 7 allow the electrodes for the sensor 206 to exit downward through the substrate 201. Electrical measurement equipment can then be attached to the back side of the sensor. Without the TSVs, electrodes could be deposited on top of the substrate. However, such deposited electrodes can create topographical variations. The topographical variations can create the possibility of leakage underneath the edge of the chamber 203 where the electrode meets the o-ring 202. With the TSVs 207, topographical discontinuities due to the electrodes can be avoided across and/or near the o-ring 202 perimeter. By avoiding topographical discontinuities, the o-ring seal can form tightly with the substrate, which can reduce the chance of fluid leakage.

Figure 3A:
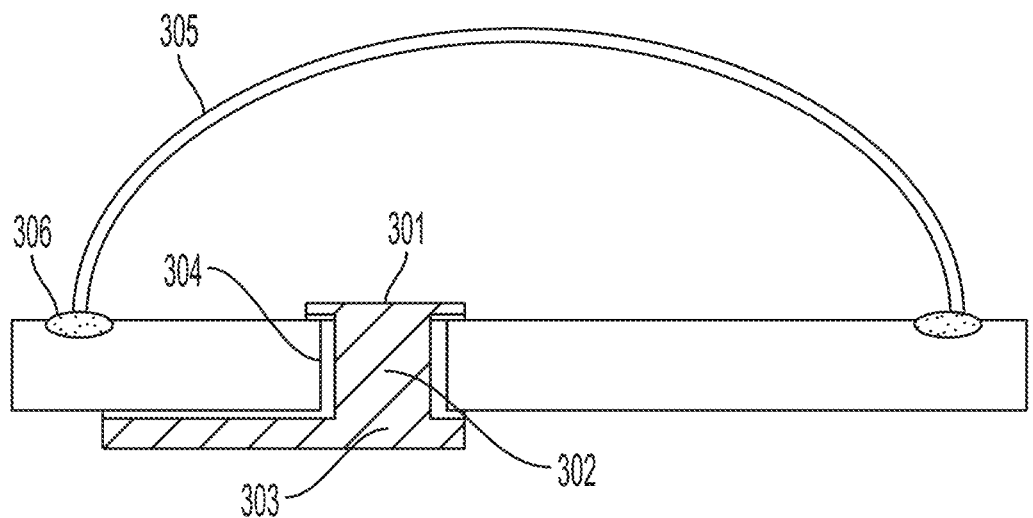
FIGS. 3A and 3B are cross-sectional and perspective schematics, respectively, of an exemplary TSV, according to some embodiments.
Figure 3B:
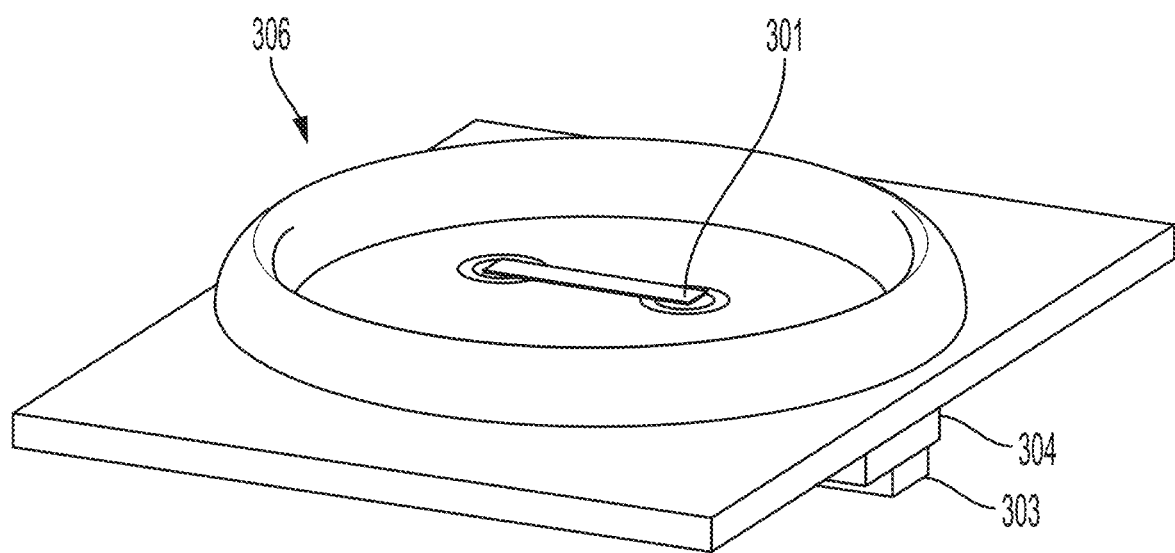

As described herein, TSVs can enable a continuous tight seal around the interface between the fluid chamber and substrate. FIGS. 3A and 3B are cross-sectional and perspective schematics, respectively, of a TSV, according to some embodiments. The TSV includes the top electrode 301, which connects to the sensor; conductive pathway 302, which is a metal that passes through a hole in the substrate; a bottom bonding pad 303, to which external electronic equipment is attached; and the dielectric (e.g., insulating) spacer 304, which prevents currents from leaking from the via to the semiconductor substrate. The seal connecting the substrate to the edge of the fluid chamber 305 is uninterrupted around the path of the interface between the o-ring 306 and the substrate, creating a leak-free chamber. The TSV can also be designed to be leak-resistant. For example, to ensure a tight seal, the TSV can be completely filled with metal and dielectric, and be completely covered on both sides by metal pads.

In some embodiments, the metal for the via and the pads are the same metal, for example Au, Cu, Ag, or Al. In certain embodiments, a different metal is used for the pads, sensor electrodes, and/or via. It should be understood that the techniques described herein are not limited in terms of metal combinations or dielectric insulator materials.

The TSV can have various dimensions. In some embodiments, the TSV has a diameter smaller than 10 microns. In some embodiments, the TSV has a diameter greater between 10 and 100 microns. The techniques described herein are not limited in terms of the sizes or shapes of the TSV.

In some embodiments, the electrical leads for the sensor exit the chamber on top of the substrate where the o-ring is attached to the substrate. In such embodiments, the adhesive covers the leads to form the tight seal. In some embodiments, the o-ring may deform around the leads to form the seal between the fluid chamber and the substrate.

In some embodiments, one or more electrodes (e.g., a reference electrode, a set of reference electrodes, and/or electrodes used for electrophoretic or electroosmotic effects) also exit the chamber through a set of one or more corresponding TSVs. In some embodiments, a reference electrode is attached through a sealed hole in the chamber material. While an exemplary reference electrode 208 is shown in FIG. 2, it should be appreciated that the techniques described herein are not limited in terms of possible reference electrode configurations and/or orientations.

Figure 4:
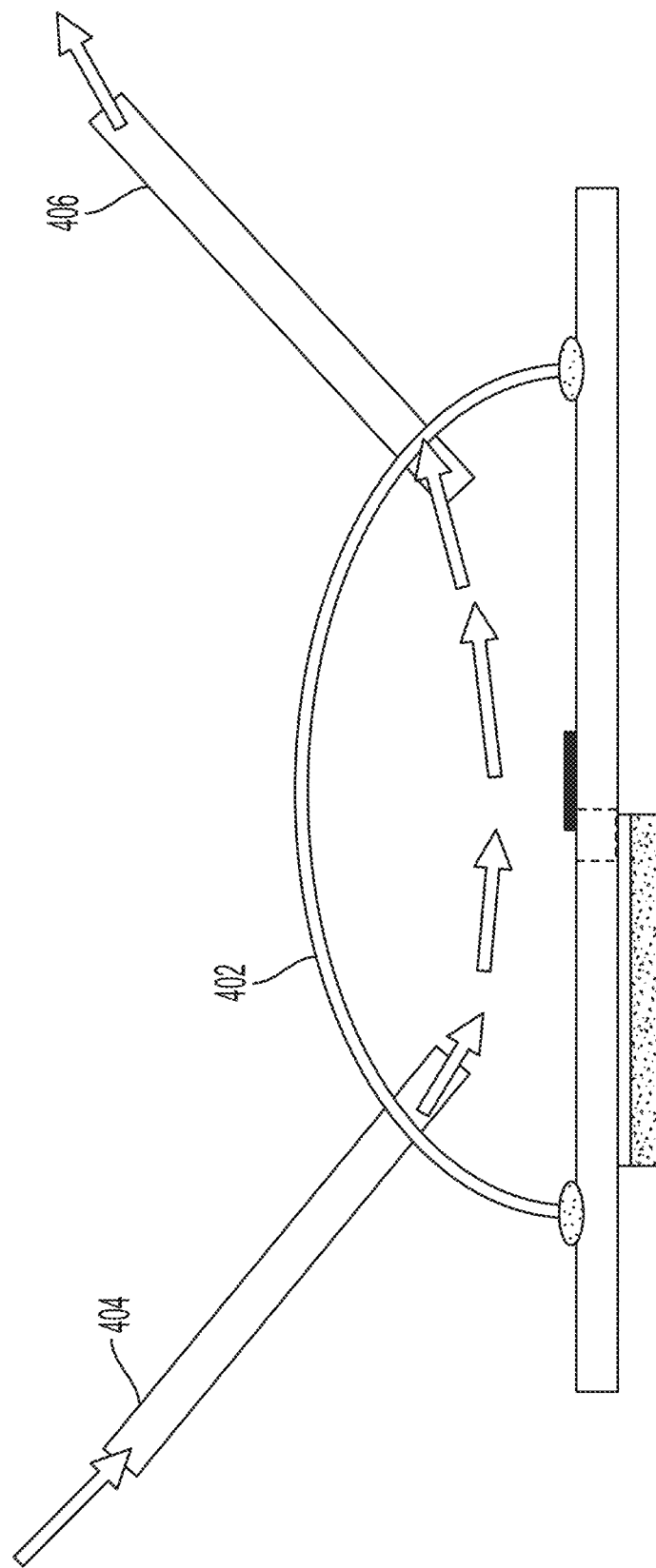
FIG. 4 is a cross-sectional view of an exemplary fluid chamber showing a fluid flow across a sensor with TSVs, according to some embodiments.

As described herein, in some embodiments the fluid chamber includes holes that are attached to fluid channels or ports. Fluid can be injected into and removed using such fluid channels, as shown in FIG. 4. FIG. 4 is a cross-sectional view of an exemplary chamber 402 showing a fluid flowing from an input port 404 to the output port 406 and over a sensor that utilizes TSVs to create electrical connections on the opposite side of the substrate. The flow rate of the fluid through the fluid chamber 402 can be controlled by controlling the pressure differential between output port 406 to input port 404. In some embodiments, the tubes are attached to a pressure-inducing mechanism and fluid reservoir. In such examples, the flow speed can be controlled by controlling the pressure differential at the ends of the input and output ports 404, 406. The total flow volume can be controlled based on the time during which flow occurs for a given fluid.

The fluid channels can be configured of various sizes, shapes and materials. In some embodiments, the tubes are greater than 1 mm in diameter. In some embodiments, the tubes are 1 micron to 1 mm in diameter. In some embodiments, the tubes are a polymer, such as polyethylene. In some embodiments, the tubes are silicone rubber. In some embodiments, the tubes are hypodermic needles. While some examples are provided herein, the techniques are not intended to be limited in terms of sizes, shapes or materials of the fluid channels.

Various fluid reservoir configurations can be used in conjunction with the fluid channels described herein. For example, fluid can be supplied into the fluid chamber from an input reservoir (e.g., through an input channel) and exit from the fluid chamber to an output reservoir (e.g., through an output channel). In some embodiments, the reservoirs are the same (e.g., with a pumping mechanism at one end of the reservoir and a return at the other end of the reservoir). As another example, the fluid channel tubes can be connected to one or more syringes from which fluid is supplied. In such examples, a pressure differential can be created by depressing the syringe. While some examples have been provided herein, the techniques should not be limited in terms of possible reservoir or pumping mechanisms/configurations.

Figure 5A:
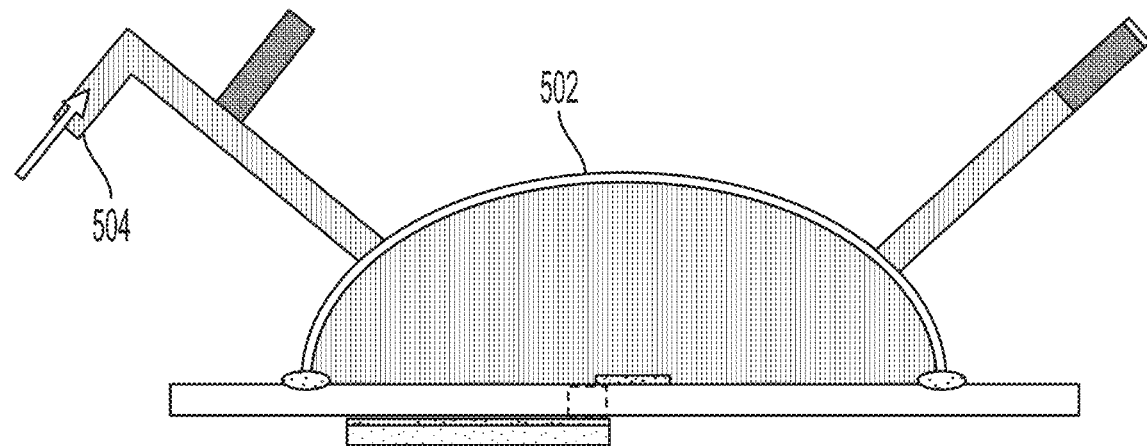
FIG. 5 is a diagram showing an exemplary fluid chamber disposed over a sensor with TSVs that is configured to allow for multiple fluids to be introduced into the fluid chamber, according to some embodiments.
Figure 5B:
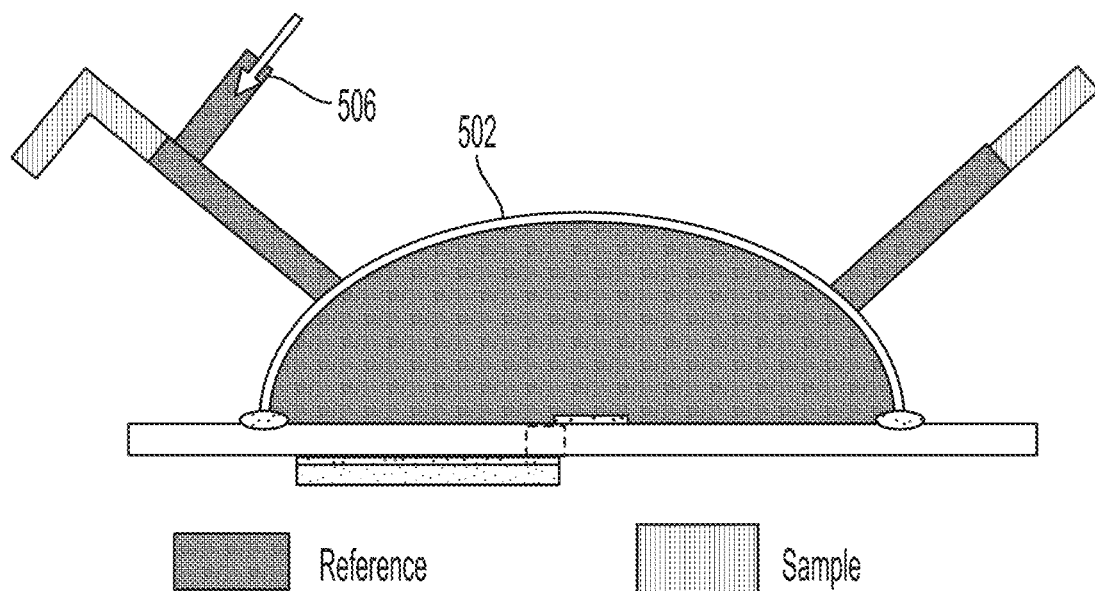

In some embodiments, multiple solutions can be used with a single device. For example, a separate reservoir and pressure source can be used to inject sample fluid(s), and reference fluid(s), and/or cleaning solution(s). FIG. 5 is a diagram of an exemplary embodiment of a fluid chamber 502 disposed over a sensor utilizing TSVs that is subject to multiple fluids, according to some embodiments. As shown in view (A), a sample fluid is first introduced into the fluid chamber 502 via inlet 504. Then, as shown in view (B), a reference fluid is introduced into the chamber via inlet 506. By introducing both the sample fluid and the reference fluid to the sensor, changes in electrical properties of the sensor can be measured relative to the reference signal, which can increase sensitivity. In some embodiments, the sample and reference fluids can be cycled. Such a technique can reduce the chance of false positive or negative determinations due to, for example, thermal drift, noise, and/or other external factors.

In some embodiments, a reusable sensor can be provided by flowing a cleaning fluid (e.g., from a cleaning fluid reservoir) into the fluid chamber to remove residue of a sample previously introduced into the fluid chamber. After cleaning the sensor, a new sample can be input into the chamber. A chamber with pressure-induced flow as described herein can provide a repeatable cleaning process, which allows a single sensor to be reused for multiple tests and/or samples. Without such techniques (e.g., without a chamber configured according to the techniques described herein) the measurements for each sensor can be limited. For example, without such techniques, only one sample is measurable per sensor device, or large-scale, possibly detrimental, cleaning may need to be used for multiple measurements.

Some embodiments relate to using a planarization layer to seal the fluidic chamber to the sensor substrate. A tight, leak-resistant seal can be achieved by using a planarized layer that is overlaid above the electrodes and substrate where the o-ring makes contact. A planarized layer can reduce and/or eliminate discontinuities in the substrate topography due to, e.g., electrodes deposited on the surface. Reducing discontinuities in the substrate topography can reduce and/or eliminate leakage of the fluid between the fluid chamber and the substrate. In some embodiments, as described herein the chamber can include input and output holes through which fluid can be injected and removed. As also described herein, the chamber can be attached to one or more pressure flow inducing devices and/or fluid reservoirs.

Figure 6:
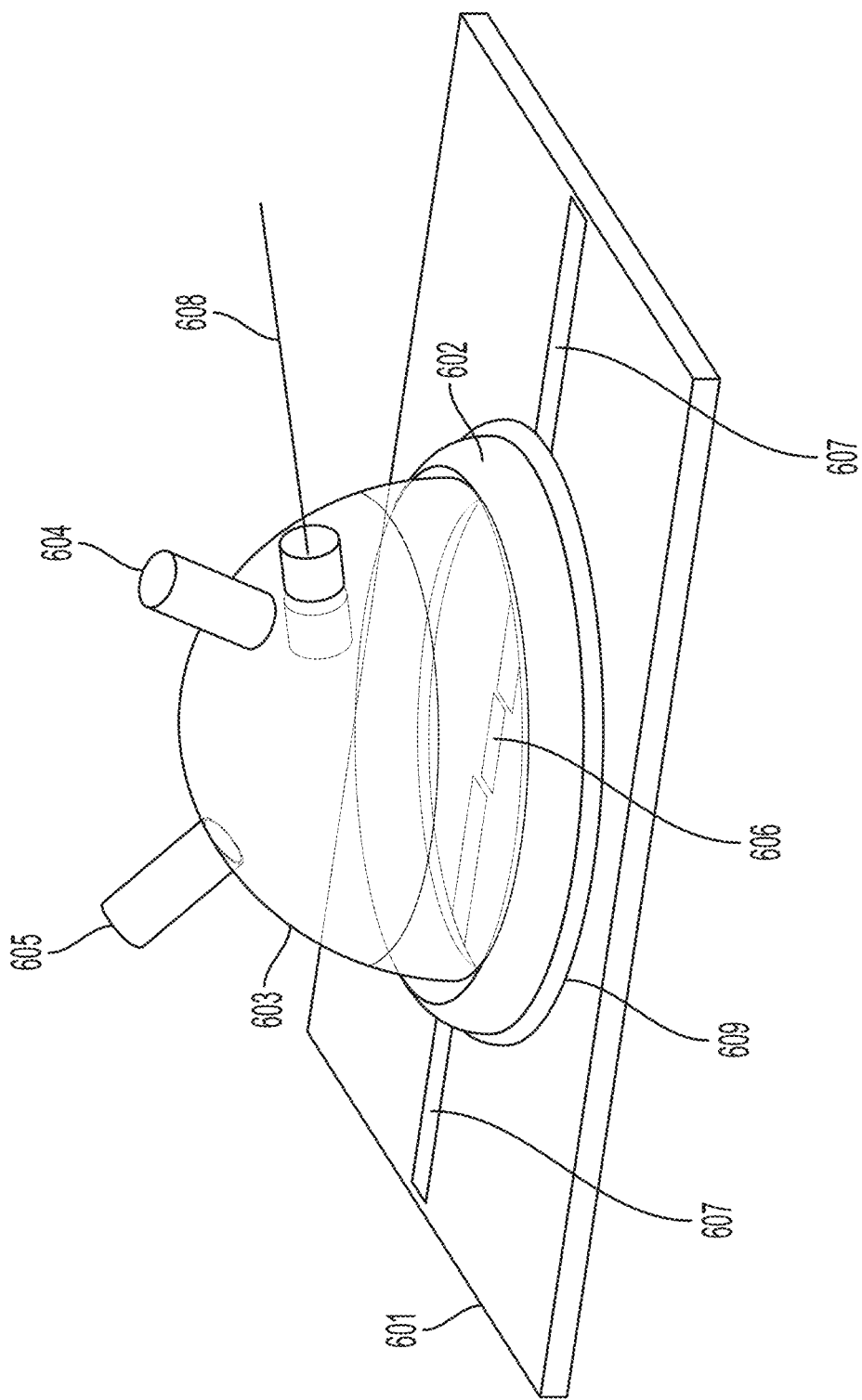
FIG. 6 is a diagram of a perspective view of an exemplary sensor with a fluid chamber that is sealed onto the sensor substrate using a planarization layer, according to some embodiments.

FIG. 6 is a diagram of an exemplary perspective view of a sensor with a fluid chamber that utilizes a planarization layer, according to some embodiments. The configuration in FIG. 6 includes some components discussed in conjunction with FIG. 2. In particular, as shown in FIG. 6, an o-ring seal 602 is adhered to the substrate 601, forming a tight seal between the chamber 603 and the o-ring 602 so that no fluid can escape between the chamber 603 and the substrate 601. An input channel 604 and an output channel 605 are attached to the chamber material, which includes holes that allow fluid to be input and output through the input channel 604 and output channel 605. A reference electrode 608 may be added through the chamber wall.

The sensor 606 is disposed in the center of the chamber 603. As shown in FIG. 6, the electrodes 607 for the sensor 606 are disposed on/contained on the top of the sensor substrate 601. Ports for attaching to other circuitry and/or external electrical measurement equipment can therefore be disposed on the same side of the chip as the sensor 603. With a geometry such as that shown in FIG. 6 with the electrodes 607 disposed on the top of the substrate 601, the surface topography of the top of the substrate typically changes as it crosses an electrode. The electrodes 607 can be up to 3 microns thick, and may include various physical features (e.g., sharp corners, bumps, etc.), creating the possibility of micro leakage sites where the o-ring 602 meets an electrode and/or electrode edge(s) in the substrate.

In some embodiments, as shown in FIG. 6, a planarized sealing layer 609 can be added onto the substrate 601. In some embodiments, the sealing layer 609 is an insulator. Exemplary materials for the sealing layer 609 can include, but are not limited to, $SiO_2$ and $Al_2O_3$. In some embodiments, a polymer or silicone is used for the sealing layer 609. The sealing layer 609 can be deposited as a layer (e.g., as a thick layer) over the surface of the chip (e.g., including over the surface of the substrate 601, electrodes 607, and/or any other components) and planarized to create a smooth top surface upon which the o-ring 602 can form a tight seal.

Figure 7:
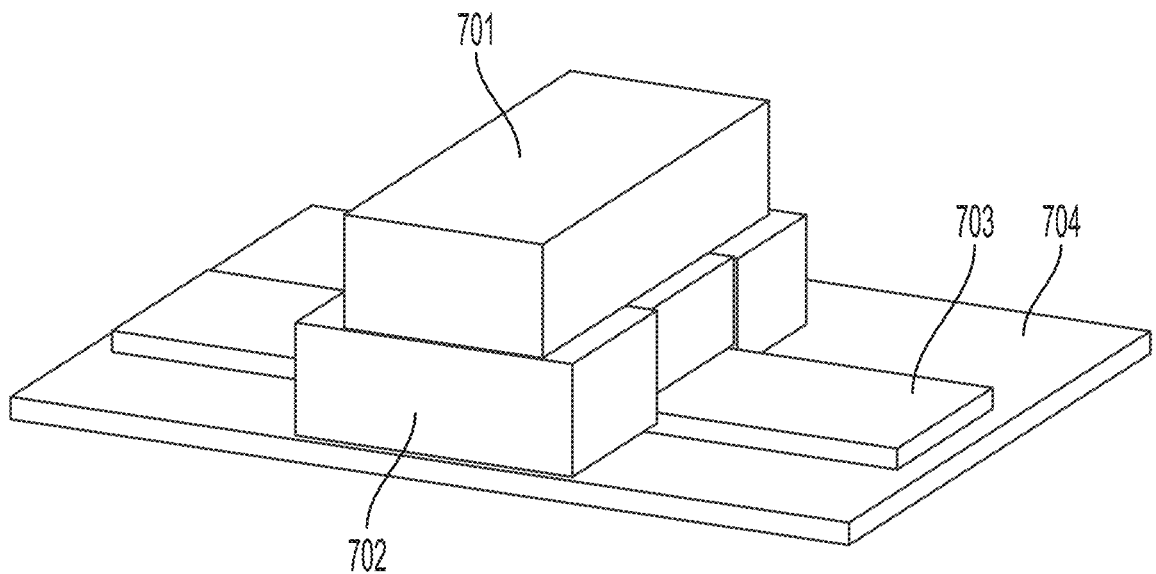
FIG. 7 is a diagram of a close-up view of a portion of an o-ring disposed on a planarized sealing layer, according to some embodiments.

FIG. 7 is a diagram of a close-up view of a portion of the o-ring 701 on the planarized sealing layer 702, according to some embodiments. As shown, the planarized layer 702 is flat on its top surface but conforms to and makes space on the bottom surface for electrode 703, creating a tight seal around the junction between the electrode 703 and the substrate 704.

Various fabrication processes can be used to achieve a planarized sealing layer. In some embodiments, the process can include defining the area of o-ring contact. In some examples, photolithography can be used to deposit a thick photoresist and define a ring. The thickness of the photoresist can be configured such that the thickness is greater than the topographical difference between discontinuities in the surface, such as discontinuities between the metal used in the electrodes and the substrate. The photoresist within the ring can be removed through developing. The planarized sealing layer, formed as a ring, can have inner and outer diameters selected so that the thickness of the ultimate ring-shaped planarized sealing layer is enough to support the o-ring. Once the ring is formed (or other shape to match the edge of the fluid chamber, as described herein), the insulating material for the planarized layer can be deposited across the entire area. The material can be deposited such that it is thick enough to form a continuous layer above the substrate and electrodes. In some embodiments, the seal material is an oxide, including but not limited to $Al_2O_3$ or $SiO_2$. In some embodiments, the seal material is a polymer. In some embodiments, the seal material may be a metal.

The seal material can be of various physical configurations. For example, the seal material can be configured such that the layer is at least 10 microns thicker than the electrodes. Some embodiments can use a thicker insulating layer, e.g., up to or greater than 100 microns. The insulator can then be planarized. Lift-off can be used to remove the insulator and photoresist in the regions where the device must be open.

Various types of planarization processes can be used. In some embodiments, mechanical planarization is used. In some embodiments, chemical-mechanical planarization is used.

In some embodiments, one or more other electrodes can exit the fluid chamber. For example, a reference electrode, a set of reference electrodes, and/or electrodes used for electrophoretic and/or electroosmotic effects, can exit the chamber through a set of associated TSVs and/or via electrodes on top of the surface of the substrate. As described herein, the reference electrode 608 can be attached through a sealed hole in the chamber material.

Figure 8:
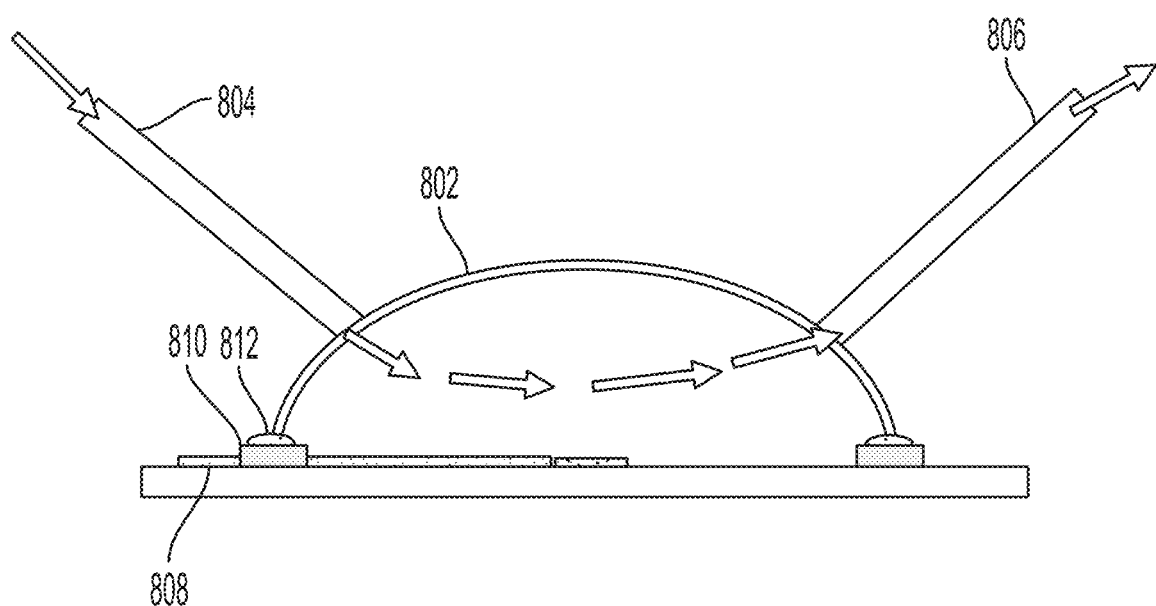
FIG. 8 is a cross-sectional view of an exemplary chamber showing a fluid flow across a sensor with electrodes disposed on the surface of the chip, according to some embodiments.

As described in conjunction with FIG. 4, input and/or output channels can be attached to the fluid chamber through which fluid can be injected and removed from the fluid chamber. FIG. 8 shows a similar configuration as that described in conjunction with FIG. 4 with a fluid chamber 802, an input channel 804 and an output channel 806, disposed on a sensor with an electrode configuration with at least one electrode 808 disposed on the top surface of the chip. As also shown in FIG. 8, the sensor configuration includes a planarized sealing layer 810 on top of which the o-ring 812 is sealed.

Figure 9:
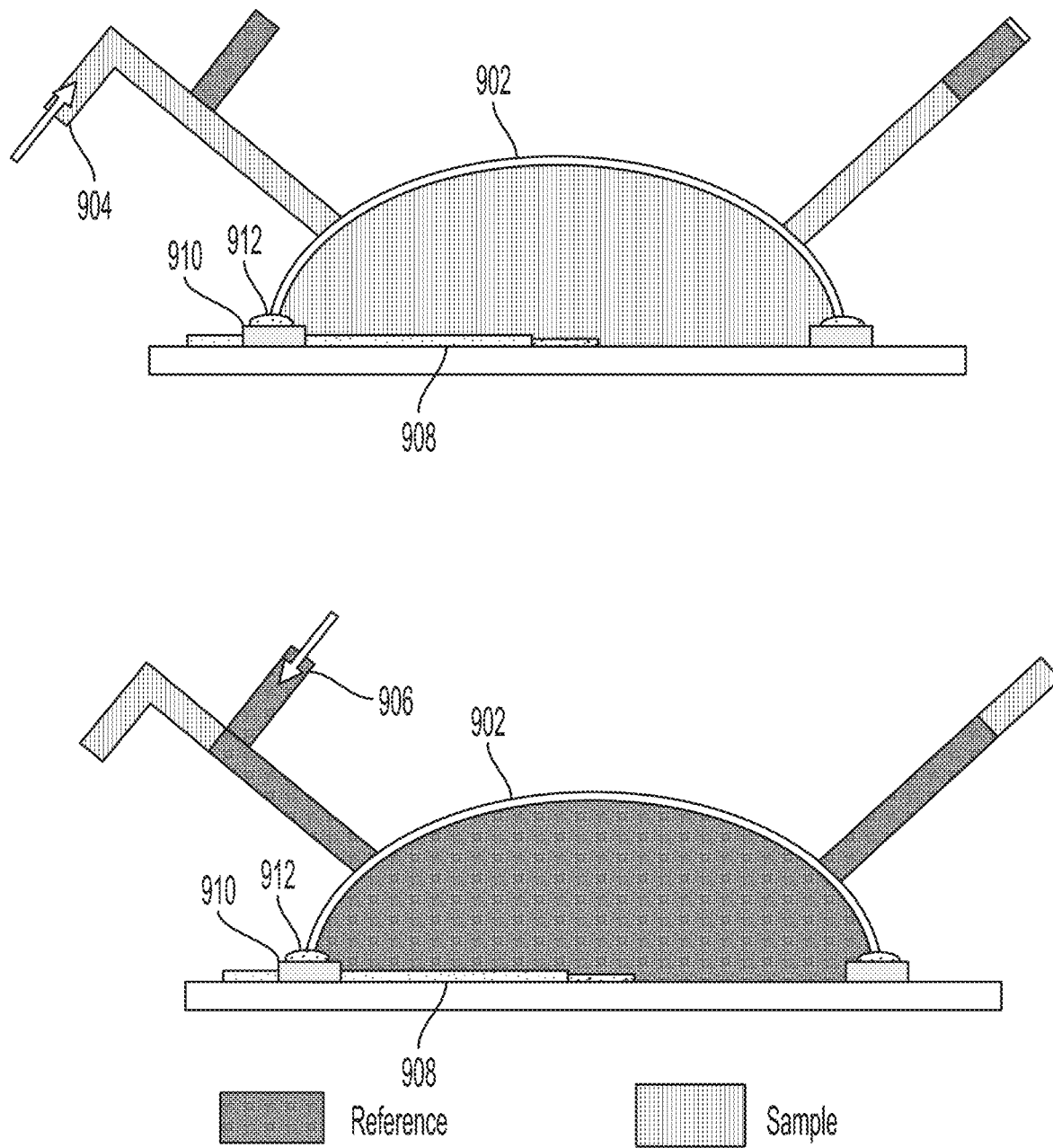
FIG. 9 is a diagram showing an exemplary fluid chamber disposed over a sensor with electrodes disposed on the surface of the chip, which is configured to allow for multiple fluids to be introduced into the fluid chamber, according to some embodiments.

As described in conjunction with FIG. 5, in some embodiments multiple reservoirs and/or pressure sources can be used for injecting sample and reference fluids. FIG. 9 shows a similar configuration as that described in conjunction with FIG. 5, with a fluid chamber 902, and two different input ports 904 and 906, which are used to pump a sample and reference fluid, respectively, into the fluid chamber 902. In the example shown in FIG. 9, the fluid chamber configuration is disposed on a sensor with an electrode configuration with at least one electrode 908 disposed on the top surface of the chip. As also shown in FIG. 9, the sensor configuration includes a planarized sealing layer 910 on top of which the o-ring 912 is sealed.

As described herein, nanowire field-effect transistor (FET) biosensors can include an array of semiconductor nanowires that have been functionalized such that a detection molecule is bound to the semiconductor surface. The detection molecule binds to a specific molecule of interest, which causes changes in electrical properties of the sensors (e.g., a conductance change in the nanowire array). It is often desirable to be able to detect multiple and/or a variety of analytes in a single sample, such as for diagnostic purposes. Detecting multiple analytes can reduce the likelihood of false positives or negatives in a diagnosis, as some diseases contain multiple markers. Additionally or alternatively, it may be desirable to run tests for the same analyte on multiple sensors, such as to reduce the possibility of false positives or negatives and/or to provide checks for false positives or negatives.

The inventors have appreciated that the sensor signal can depend on one or more environmental factors. These factors can include, but are not limited to: temperature, which can determine the analyte binding properties and/or semiconductor conduction properties; background ionic concentration of the fluid, which can affect analyte charge and binding properties; pH, which can affect analyte binding properties and protein structure; reference or background potential within the fluid, which can modify the measured conductance of the nanowire array through field effects; and/or electric fields, which can affect the analyte locations, charge distributions, and/or mobility. The inventors have therefore determined that it can be desirable to control and/or measure such properties for the same sample, which can improve diagnostic capabilities.

It can be desirable to run multiple tests on the same sample because it can reduce the amount of sample needed compared to tests that require many different samples. For example, limiting the sample size can be very important for bodily fluids such as blood, which can require painful extraction and/or the loss of which can be detrimental to health. Using a single sample can also reduce the impact of time sensitive biological processes and/or bodily processes on a diagnosis.

In some embodiments, the techniques described herein provide for a multi-chip module (MCM) for nanowire FET biosensors. A MCM can include multiple devices integrated onto a single framework. As described herein, the devices can include nanowire FET biosensors and any set of technology that measures other sample properties, including but not limited to ionic concentration, conductivity, temperature, pH, and/or the presence of other analytes.

The multiple MCM sensors can operate in various configurations, including operating in sequence or in parallel for use in measuring multiple analyte concentrations and/or other characteristics of a sample. In some embodiments, a number of nanowire FET biosensors are functionalized to be sensitive to a single analyte. In such embodiments, the MCM can include a number of individual devices placed on a single substrate, where each individual device is functionalized to be sensitive to the one given analyte. Some embodiments can incorporate fluid modification, including but not limited to cell removal, desalting, and or other fluid modifications. Some embodiments incorporate non-analyte detection modules, including but not limited to background conductivity, temperature, and/or other detection modules. While some examples have been provided herein, the techniques described herein are designed to cover any such multisensory configurations.

Single-device functionalization in the MCM can provide one or more improvements over other possible arrangements. For example, a different arrangement can include the placement of multiple sensors on the same chip. However, functionalization of such an arrangement can be complex and may be unrepeatable. For such an arrangement, the configuration would typically require either: (a) separating the functionalizing fluid into multiple very small individual portions, one for each analyte, and controllably place the small portions over each sensor; or (b) controllably preventing individual functionalization as different functionalizing fluids are sequentially contacted with all of the sensors. However, choice (a) can be prohibitive due to size limitations, such as for an integrated sensor for use with a small volume of test fluid. Choice (b) can be prohibitive due to repeatability and/or technological issues with attempting to selectively prevent functionalization.

Figure 10:
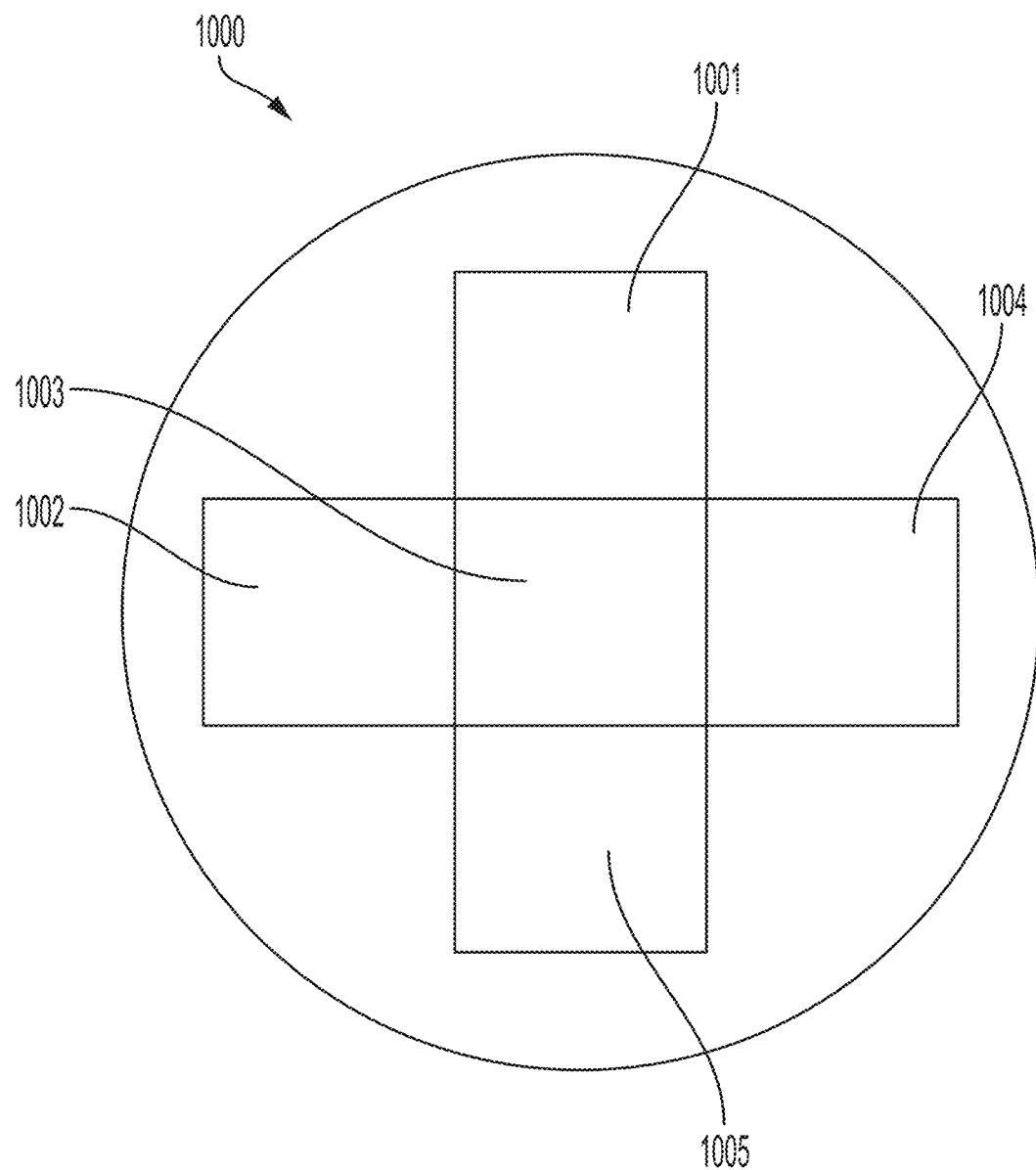
FIG. 10 is a schematic diagram of an exemplary wafer showing different regions that can be manufactured with different functionalities, according to some embodiments.

The techniques described herein can address these and/or other problems with using multiple sensors on a single chip. As described herein, the techniques include integrating multiple chips onto a single substrate after functionalization. This can allow for functionalization at the wafer level, or for a large portion of a single wafer. Therefore, a large portion of a single wafer of identical devices can be functionalized to be sensitive to a given analyte. FIG. 10 is a schematic of a wafer showing different regions that can be manufactured with different functionalities, according to some embodiments. For example, the different regions can be functionalized to be sensitive to different analytes, to contain devices with other functionalities (e.g., such as fluid conductance measurement), and/or the like. FIG. 10 shows a complete wafer 1000 with different regions (1001, 1002, 1003, 1004, and 1005) dedicated to different analytes. The individual devices can then be removed, post-functionalization, and placed on a new substrate to create a new single chip sensitive to multiple analytes. The wafer can be diced either before or after functionalization. In some embodiments, additional functionality, such as conductance and/or temperature measurements, can be used instead of and/or in addition to analyte sensors in the single devices.

Figure 11A:
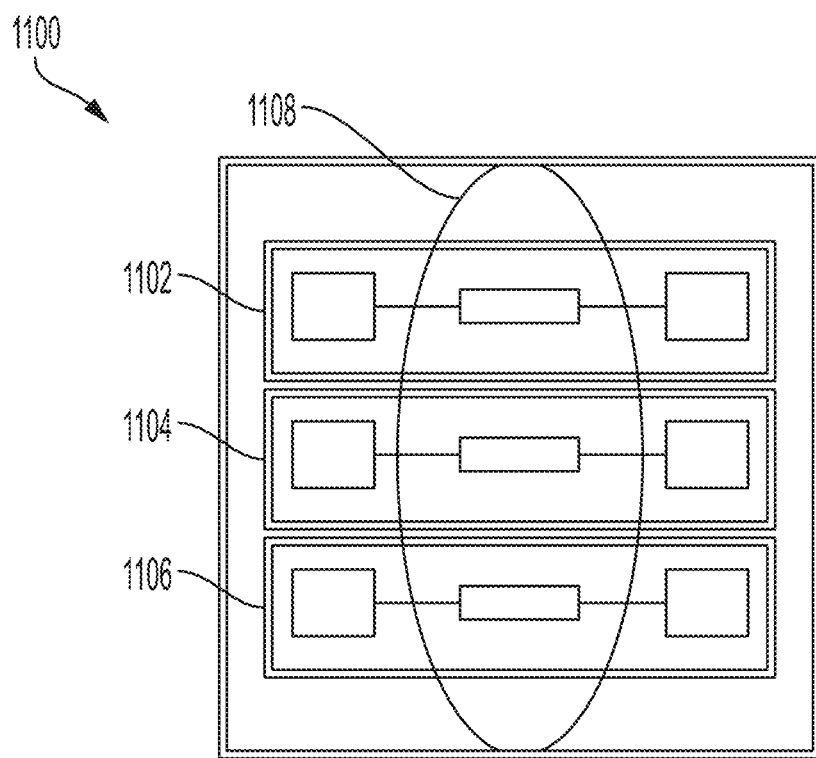
FIG. 11A is a schematic diagram of an exemplary three-sensor multiple-chip module (MCM) with simultaneous fluid measurement capabilities, according to some embodiments.
Figure 11B:
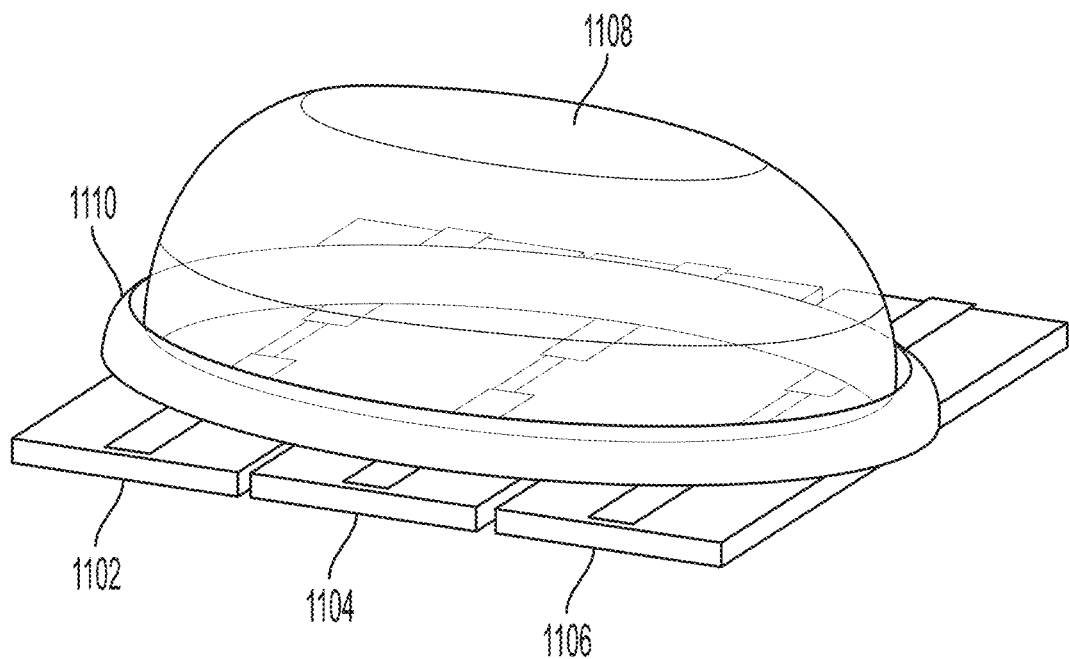
FIG. 11B is a three-dimensional perspective view of the three-sensor MCM of FIG. 11A, according to some embodiments.

In some embodiments, the individual chips can be configured to measure a fluid sample simultaneously. For example, the individual chips can be configured such that the chips are small enough and placed close enough together so that a single fluid sample can be measured simultaneously. FIG. 11A is a schematic diagram of an exemplary three-sensor MCM 1100 with simultaneous fluid measurement capabilities, according to some embodiments. FIG. 11B is a three-dimensional perspective view of the three-sensor MCM 1100 of FIG. 11A, according to some embodiments. The MCM includes three sensors 1102, 1104 and 1106. The three different sensors are encapsulated in the same fluid chamber 1108. The separate chips for each sensor are attached together in a manner that creates a leak-resistant seal over the chips and the interchip seams. As shown in this example, an o-ring 1110 is used to create a leak-resistant seal over the chips and the interchip seams (e.g., as described in conjunction with FIGS. 2-5). However, it should be appreciated that other techniques can be used to seal the fluid chamber onto the multiple chips. For example, a planarized layer can be used to seal the fluid chamber onto the multiple chips, as described in conjunction with FIGS. 6-9.

Figure 12A:
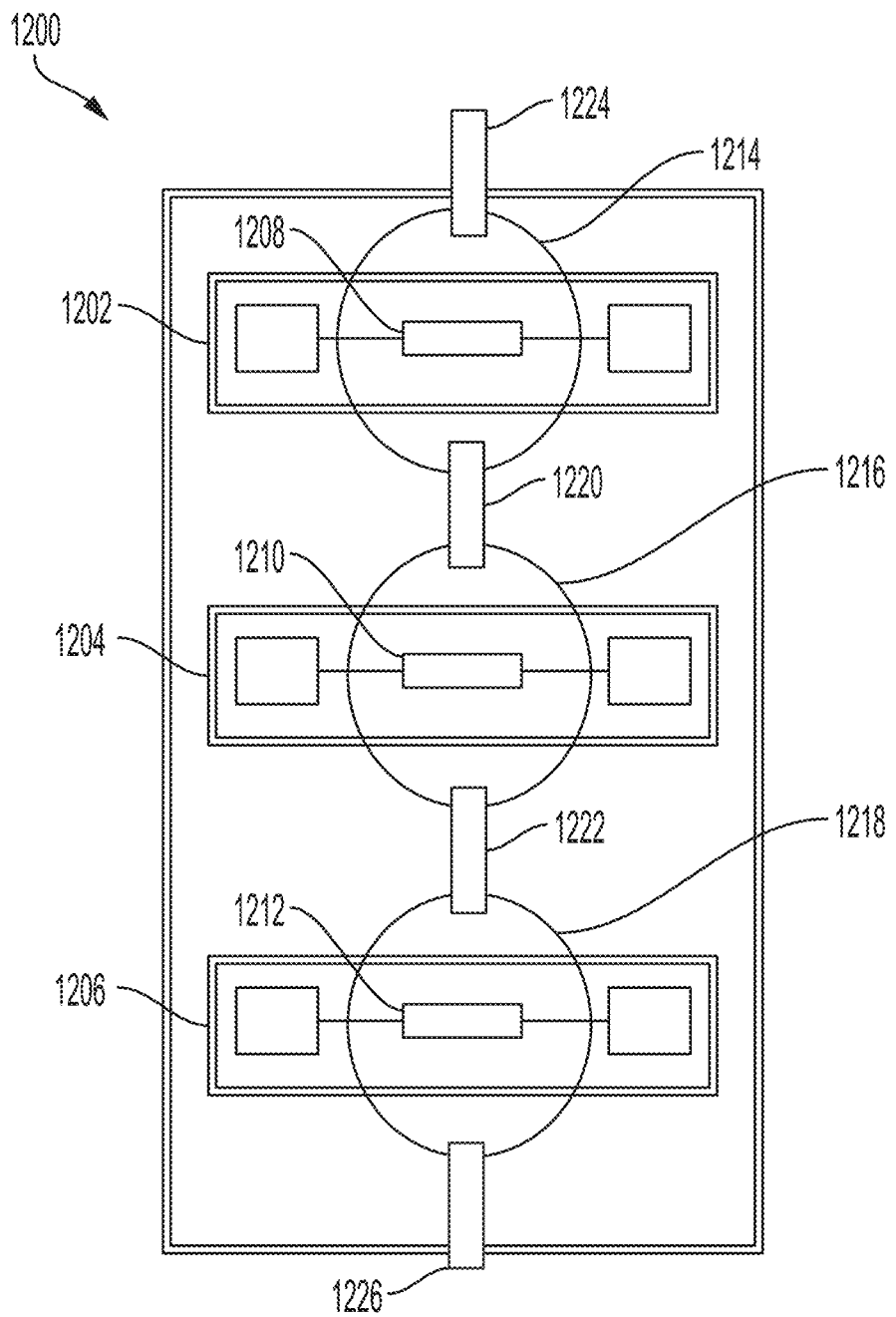
FIG. 12A is a schematic of an exemplary three-sensor MCM with a configuration to provide sequential measurement, according to some embodiments.
Figure 12B:
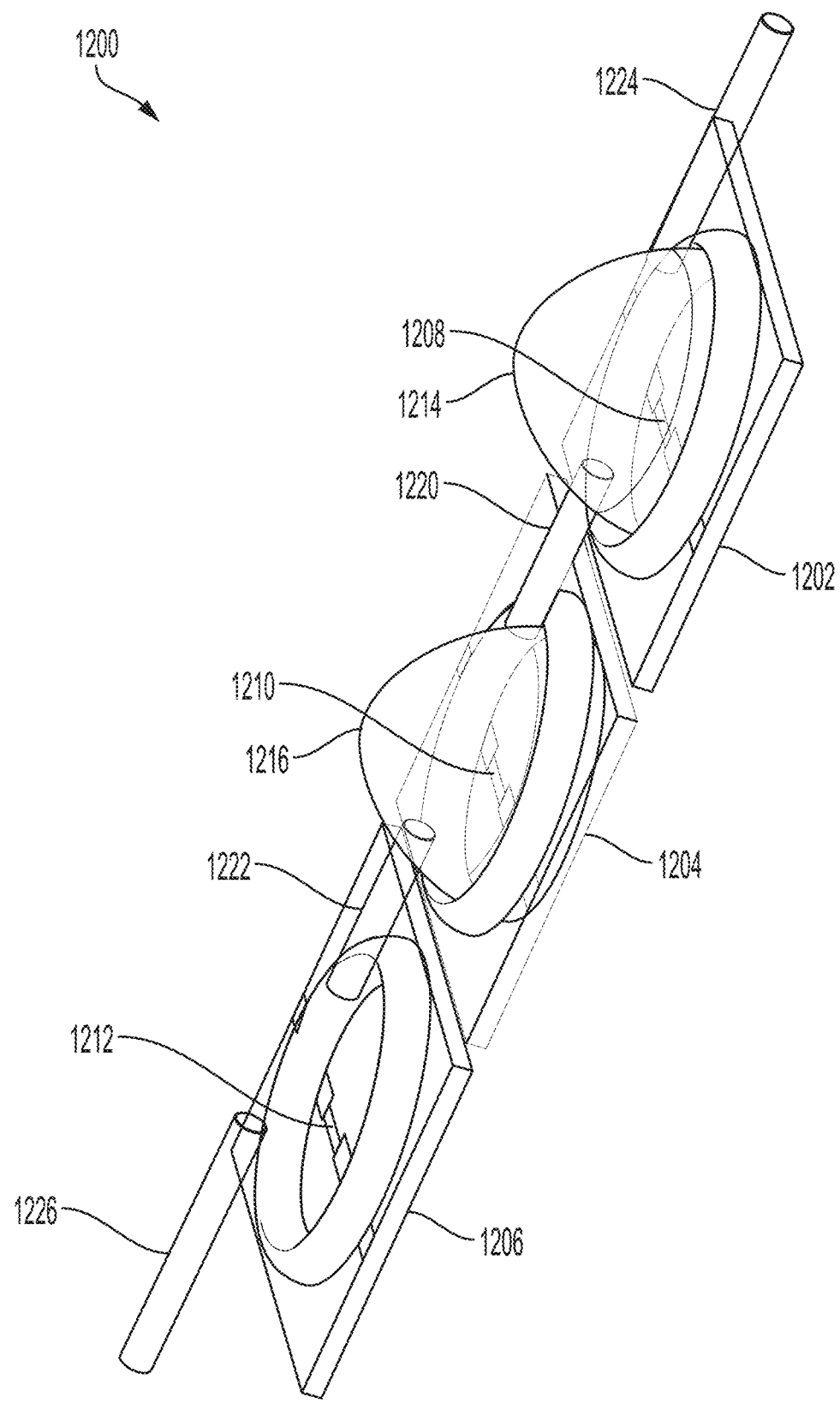
FIG. 12B is a three-dimensional perspective view of the three-sensor MCM of FIG. 12A, according to some embodiments.

In some embodiments, the individual chips can be arranged in series and the single fluid sample can be flowed sequentially over each individual sensor. In some embodiments, the chips can be arranged in series by using individual, connected sealed fluid chambers over each sensor. FIG. 12A is a schematic of an exemplary three-sensor MCM 1200 with a sequential measurement configuration, according to some embodiments. FIG. 12B is a three-dimensional perspective view of the three-sensor MCM 1200 of FIG. 12A, according to some embodiments. The MCM 1200 includes three sensor chips 1202, 1204 and 1206, which each have corresponding sensors 1208, 1210, and 1212. Each sensor is disposed in a different fluid chamber, such that sensor 1208 is disposed in fluid chamber 1214, sensor 1210 is disposed in fluid chamber 1216, and sensor 1212 is disposed in fluid chamber 1218. As shown in this example, an o-ring is used to create a leak-resistant seal between each chip and its associated fluid chamber (e.g., as described in conjunction with FIGS. 2-5). However, it should be appreciated that other techniques can be used to seal the fluid chamber onto the multiple chips. For example, a planarized layer can be used to seal the fluid chamber onto the multiple chips, as described in conjunction with FIGS. 6-9.

The fluid chambers are connected through fluid channels. Fluid channel 1220 connects fluid chambers 1214 and 1216, and fluid channel 1222 connects fluid chambers 1216 and 1218. Input fluid channel 1224 connects to fluid chamber 1214 (which is omitted from FIG. 12B for illustrative purposes), and output fluid channel 1226 connects to fluid channel 1218.

The exemplary configuration shown in FIGS. 12A-12B allows a sample to be introduced to fluid chamber 1214 via fluid channel 1224 (e.g., from a fluid reservoir) so that the sample flows over sensor 1208. The sample sequentially flows from fluid chamber 1214, through fluid channel 1220, and into fluid chamber 1216 over sensor 1210. The sample then sequentially flows from fluid chamber 1216, through fluid channel 1222, into fluid chamber 1218 over sensor 1212. The sample can flow out of fluid chamber 1218 through fluid channel 1226 (e.g., into a reservoir). As described herein, various types of sensors and/or other functional components can be used for the individual chips. Such a configuration can be useful, for example, for sequential modification and testing of a sample. For example, the first module may desalt the sample, the next module can measure the conductivity to verify desalting, and then subsequent module(s) can test for analytes. Therefore, it should be appreciated that while FIGS. 12A-12B show an exemplary embodiment with three biosensor chips, other embodiments and combinations of devices to achieve sequential and simultaneous measurements may also be employed according to the techniques described herein.

In some embodiments, individual resistance measurements can be made for each module. In some embodiments, the resistance of all modules can be measured simultaneously with a single meter. In some embodiments, the resistance meter is integrated with the sensors onto the MCM. In some embodiments, the resistance meters are external to the MCM and can include, for example, external wiring and/or wireless powering. The techniques described herein are therefore not limited in terms of such measurement set-ups.

Various computer systems can be used to perform any of the aspects of the techniques and embodiments disclosed herein. The computer system may include one or more processors and one or more non-transitory computer-readable storage media (e.g., memory and/or one or more non-volatile storage media) and a display. The processor may control writing data to and reading data from the memory and the non-volatile storage device in any suitable manner, as the aspects of the invention described herein are not limited in this respect. To perform functionality and/or techniques described herein, the processor may execute one or more instructions stored in one or more computer-readable storage media (e.g., the memory, storage media, etc.), which may serve as non-transitory computer-readable storage media storing instructions for execution by the processor.

In connection with techniques described herein, code used to, for example, provide the techniques described herein may be stored on one or more computer-readable storage media of computer system. Processor may execute any such code to provide any techniques for planning an exercise as described herein. Any other software, programs or instructions described herein may also be stored and executed by computer system. It will be appreciated that computer code may be applied to any aspects of methods and techniques described herein. For example, computer code may be applied to interact with an operating system to plan exercises for diabetic users through conventional operating system processes.

The various methods or processes outlined herein may be coded as software that is executable on one or more processors that employ any one of a variety of operating systems or platforms. Additionally, such software may be written using any of numerous suitable programming languages and/or programming or scripting tools, and also may be compiled as executable machine language code or intermediate code that is executed on a virtual machine or a suitable framework.

In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the present invention. The non-transitory computer-readable medium or media may be transportable, such that the program or programs stored thereon may be loaded onto any computer resource to implement various aspects of the present invention as discussed above.

The terms "program," "software," and/or "application" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion among different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in non-transitory computer-readable storage media in any suitable form. Data structures may have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more methods, of which examples have been provided. The acts performed as part of a method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This allows elements to optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

Various aspects are described in this disclosure, which include, but are not limited to, the above-described aspects.

The invention claimed is:

1. A device, comprising:
a sensor chip comprising a set of sensor elements at least partially disposed on a surface of a substrate, wherein each sensor element of the set of sensor elements is configured to sense an analyte, and the set of sensor elements comprise an associated set of electrodes extending along the surface of the substrate;
a fluid chamber extending vertically from the substrate and having an outer hemispheric surface exposed to the environment, the fluid chamber comprising an edge proximate to the surface of the substrate, the fluid chamber comprising an inner portion in fluid communication with the set of sensor elements, wherein at least one electrode of the set of electrodes extends from the inner portion of the chamber across the edge of the chamber and outside of the fluid chamber; and
a sealing member between the edge of the fluid chamber and the surface of the substrate such that the sealing member is disposed over at least a portion of the electrode that extends across the edge of the fluid chamber.

2. The device of claim 1, wherein the set of sensor elements comprise a silicon sensor.

3. The device of claim 2, wherein the set of sensor elements comprise a plurality of silicon sensors.

4. The device of claim 3, wherein a sensor element of each set of sensor elements comprises a source, a drain, and at least one nanowire in electrical communication with the source and the drain.

5. The device of claim 4, wherein the set of electrodes comprises a first electrode in electrical communication with the source, and a second electrode in electrical communication with the drain.

6. The device of claim 1, wherein the set of sensor elements are functionalized to detect an analyte.

7. The device of claim 1, further comprising a fluid channel in fluid communication with the fluid chamber.

8. The device of claim 7, wherein the fluid channel is a tube that fluidly connects a fluid reservoir to the fluid chamber.

9. The device of claim 7, further comprising a second fluid channel in fluid communication with the fluid chamber.

10. The device of claim 9, wherein the fluid channel is an input fluid channel and the second fluid channel is an output fluid channel.

11. The device of claim 1, wherein the sealing member comprises a planarized layer disposed on the surface of the substrate and the portion of the electrode extending across the edge of the fluid chamber.

12. The device of claim 11, wherein the planarized layer comprises a material selected from the group consisting of an oxide, a polymer, and a metal.

13. The device of claim 11, wherein the sealing member comprises a bottom portion contoured over the surface of the substrate and the portion of the electrode extending across the edge of the fluid chamber.

14. The device of claim 11, wherein the sealing member comprises an o-ring.

15. The device of claim 14, wherein the o-ring is disposed between the planarized layer and the edge of the fluid chamber.

16. The device of claim 14, wherein the o-ring comprises a material selected from the group consisting of a permanent glue, a gel, a polymer, rubber and silicone.

17. The device of claim 14, wherein the planarized layer and o-ring comprise a leak-resistant seal between the edge of the fluid chamber and the top surface of the substrate and the portion of the electrode.

* * * * *